US012290608B2

(12) United States Patent
Derrick et al.

(10) Patent No.: US 12,290,608 B2
(45) Date of Patent: May 6, 2025

(54) LAYERED COLLAGEN DRESSING WITH EXTENDED BACTERIA AND BIOFILM REDUCING CAPABILITIES

(71) Applicant: Solventum Intellectual Properties Company, Maplewood, MN (US)

(72) Inventors: Kathleen L. Derrick, San Antonio, TX (US); Kristine M. Kieswetter, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 622 days.

(21) Appl. No.: 17/623,432

(22) PCT Filed: Jun. 25, 2020

(86) PCT No.: PCT/IB2020/056046
§ 371 (c)(1),
(2) Date: Dec. 28, 2021

(87) PCT Pub. No.: WO2020/261190
PCT Pub. Date: Dec. 30, 2020

(65) Prior Publication Data
US 2022/0347339 A1    Nov. 3, 2022

Related U.S. Application Data

(60) Provisional application No. 62/868,639, filed on Jun. 28, 2019.

(51) Int. Cl.
| *A61L 15/20* | (2006.01) |
| *A61K 31/194* | (2006.01) |
| *A61L 15/18* | (2006.01) |
| *A61L 15/22* | (2006.01) |
| *A61L 15/42* | (2006.01) |
| *A61L 15/44* | (2006.01) |
| *A61L 15/64* | (2006.01) |

(52) U.S. Cl.
CPC ............ *A61L 15/20* (2013.01); *A61K 31/194* (2013.01); *A61L 15/18* (2013.01); *A61L 15/225* (2013.01); *A61L 15/42* (2013.01); *A61L 15/44* (2013.01); *A61L 15/64* (2013.01); *A61L 2300/104* (2013.01); *A61L 2300/21* (2013.01); *A61L 2300/404* (2013.01); *A61L 2300/802* (2013.01)

(58) Field of Classification Search
None
See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for Corresponding Application No. PCT/IB2020/056046, mailed Sep. 30, 2020.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.

(Continued)

*Primary Examiner* — Robert A Wax
*Assistant Examiner* — Andre Mach

(57) ABSTRACT

The present disclosure provides wound dressing compositions that disrupt biofilm formation in a wound upon application. The wound dressing composition includes a first layer comprising a homogeneous mixture of a collagen, an oxidized regenerated cellulose (ORC), and at least one bacteria reducing active ingredient and a second layer comprising a homogeneous mixture of a collagen, an oxidized regenerated cellulose (ORC), a silver compound, and at least one bacteria reducing active ingredient, and the uses thereof. Also disclosed herein are kits comprising the wound dressing compositions of the present technology, and instructions for use.

16 Claims, No Drawings

(56) References Cited

U.S. PATENT DOCUMENTS

| | | |
|---|---|---|
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | WO-2019040729 A1 * | 2/2019 ............ A61L 15/18 |

OTHER PUBLICATIONS

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

(56) References Cited

OTHER PUBLICATIONS

PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

LAYERED COLLAGEN DRESSING WITH EXTENDED BACTERIA AND BIOFILM REDUCING CAPABILITIES

TECHNICAL FIELD

The present technology relates generally to wound dressing compositions including a first layer comprising a homogeneous mixture of a collagen, an oxidized regenerated cellulose (ORC), and at least one bacteria reducing active ingredient, and a second layer comprising a homogeneous mixture of a collagen, an oxidized regenerated cellulose (ORC), a silver compound, and at least one bacteria reducing active ingredient, and the uses thereof. Kits for use in practicing the methods are also provided.

BACKGROUND

The following description of the background of the present technology is provided simply as an aid in understanding the present technology and is not admitted to describe or constitute prior art to the present technology.

Infections can retard wound healing and, if untreated, can result in tissue loss, systemic infections, septic shock, and death. Moreover, in addition to vegetative or free-floating bacteria present in a wound, bacterial biofilms may also form in a wound presenting further challenges in wound therapy, particularly chronic wounds. A biofilm comprises a polysaccharide extracellular matrix produced by an association of microorganisms (e.g., single or multiple species) that have adhered onto a surface, forming three-dimensional microbial communities. The ability of bacteria to form these complex biofilms can impede a host's defense mechanisms against pathogens. Currently, there is an unmet need for wound dressing products that can prevent, reduce, inhibit, or disrupt biofilm formation in a wound upon application, and over time.

SUMMARY OF THE PRESENT TECHNOLOGY

In one aspect, the present disclosure provides a wound dressing composition comprising a first layer and a second layer, wherein the first layer comprises a homogeneous mixture of a collagen, an oxidized cellulose, and at least one bacteria reducing active ingredient, wherein the second layer comprises a homogeneous mixture of a collagen, an oxidized cellulose, a silver compound, and at least one bacteria reducing active ingredient, and wherein the at least one bacteria reducing active ingredient of each of the first layer and of the second layer comprises at least one organic acid.

In some embodiments of the wound dressing composition, the at least one bacteria reducing active ingredient of each of the first layer and of the second layer is independently selected from the group consisting of citric acid, acetic acid, and any combination thereof. In some embodiments, the at least one the bacteria reducing active ingredient is citric acid. Additionally or alternatively, in some embodiments, the citric acid is present in a concentration of about 50 mM to about 400 mM, or about 100 mM to about 250 mM. Additionally or alternatively, in some embodiments, the citric acid of each of the first layer and of the second layer may independently be present in a concentration of about 50 mM, about 52 mM, about 54 mM, about 56 mM, about 58 mM, about 60 mM, about 62 mM, about 64 mM, about 66 mM, about 68 mM, about 70 mM, about 72 mM, about 74 mM, about 76 mM, about 78 mM, about 80 mM, about 82 mM, about 84 mM, about 86 mM, about 88 mM, about 90 mM, about 92 mM, about 94 mM, about 96 mM, about 98 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, or any range including and/or in between any two of the preceding values.

Additionally or alternatively, in some embodiments, the at least one bacteria reducing active ingredient of each of the first layer and of the second layer is mixed with a solvent, wherein the solvent is water, a ($C_1$-$C_3$)alcohol or an aqueous solution thereof. Additionally or alternatively, in some embodiments, the ($C_1$-$C_3$)alcohol comprises one or more of methanol, ethanol, propanol, isopropanol, or any combination thereof.

Additionally or alternatively, in some embodiments, the oxidized cellulose of each of the first layer and of the second layer independently comprises oxidized regenerated cellulose (ORC). Additionally or alternatively, in some embodiments, the first layer comprises about 30 wt. % to about 70 wt. % of the oxidized cellulose, with a weight-average molecular weight of about 10,000 to about 1,000,000. Additionally or alternatively, in some embodiments, the second layer comprises about 30 wt. % to about 70 wt. % of the oxidized cellulose, with a weight-average molecular weight of about 10,000 to about 1,000,000. Additionally or alternatively, in some embodiments, the oxidized cellulose of each of the first layer and of the second layer may independently comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, or any range including and/or in between any two of the preceding values. Additionally or alternatively, in some embodiments, the oxidized cellulose of each of the first layer and of the second layer may independently comprise a weight-average molecular weight of about 10,000, about 11,000, about 12,000, about 13,000, about 14,000, about 15,000, about 16,000, about 17,000, about 18,000, about 19,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 55,000, about 60,000, about 65,000, about 70,000, about 75,000, about 80,000, about 85,000, about 90,000, about 95,000, about 100,000, about 110,000, about 120,000, about 130,000, about 140,000, about 150,000, about 160,000, about 170,000, about 180,000, about 190,000, about 200,000, about 210,000, about 220,000, about 230,000, about 240,000, about 250,000, about 260,000, about 270,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 460,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, or any range including and/or in between any two of the preceding values.

Additionally or alternatively, in some embodiments, the oxidized cellulose of the first layer comprises fiber lengths of about 5 µm to about 1,000 µm. Additionally or alternatively, in some embodiments, the oxidized cellulose of the second layer comprises fiber lengths of about 5 µm to about 1,000 µm. Additionally or alternatively, in some embodiments, the oxidized cellulose of the first layer and the second layer may independently comprise fibers lengths of about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 22 µm, about 24 µm, about 26 µm, about 28 µm, about 30 µm, about 32 µm, about 34 µm, about 36 µm, about 38 µm, about 40 µm, about 42 µm, about 44 µm, about 46 µm, about 48 µm, about 50 µm, about 55 µm, about 60 µm, about 65 µm, about 70 µm, about 75 µm, about 80 µm, about 85 µm, about 90 µm, about 95 µm, about 100 µm, about 110 µm, about 120 µm, about 130 µm, about 140 µm, about 150 µm, about 160 µm, about 170 µm, about 180 µm, about 190 µm, about 200 µm, about 220 µm, about 230 µm, about 240 µm, about 250 µm, about 260 µm, about 280 µm, about 300 µm, about 320 µm, about 340 µm, about 360 µm, about 380 µm, about 400 µm, about 420 µm, about 440 µm, about 460 µm, about 480 µm, about 500 µm, about 550 µm, about 600 µm, about 650 µm, about 700 µm, about 750 µm, about 800 µm, about 850 µm, about 900 µm, about 950 µm, about 1,000 µm, or any range including and/or in between any two of the preceding values.

Additionally or alternatively, in some embodiments, the collagen of each of the first layer and of the second layer is independently a mammalian collagen. Additionally or alternatively, in some embodiments, the mammalian collagen is selected from the group consisting of a bovine collagen, a human collagen, a recombinantly derived collagen, and any combination thereof. Additionally or alternatively, in some embodiments, the first layer comprises about 0.1 wt. % to about 60 wt. %, or about 30 wt. % to about 95 wt. % of the mammalian collagen, with a weight-average molecular weight of about 5,000 to about 100,000. Additionally or alternatively, in some embodiments, the second layer comprises about 0.1 wt. % to about 60 wt. %, or about 30 wt. % to about 95 wt. % of the mammalian collagen, with a weight-average molecular weight of about 5,000 to about 100,000. Additionally or alternatively, in some embodiments, the mammalian collagen of each of the first layer and of the second layer independently comprises a weight-average molecular weight of about 5,000, about 6,000, about 7,000, about 8,000, about 9,000, about 10,000, about 12,000, about 14,000, about 16,000, about 18,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 52,000, about 54,000, about 56,000, about 58,000, about 60,000, about 62,000, about 64,000, about 66,000, about 68,000, about 70,000, about 72,000, about 74,000, about 76,000, about 78,000, about 80,000, about 82,000, about 84,000, about 86,000, about 88,000, about 90,000, about 92,000, about 94,000, about 96,000, about 98,000, about 100,000, or any range including and/or in between any two of the preceding values.

Additionally or alternatively, in some embodiments, each of the first layer and the second layer may independently comprise a ratio of collagen to ORC of about 60:40 to about 40:60. Additionally or alternatively, in some embodiments, each of the first layer and the second layer may independently comprise a ratio of collagen to ORC of about 60:40, about 55:45, about 50:50, about 45:55, about 40:60, or any range including and/or in between any two of the preceding values.

Additionally or alternatively, in some embodiments, the second layer comprises about 0.1 wt. % to about 1 wt. %, or about 0.1 wt. % to about 3 wt. % of the silver compound. Additionally or alternatively, in some embodiments, the silver compound of the second layer may comprise about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.22 wt. %, about 0.24 wt. %, about 0.26 wt. %, about 0.28 wt. %, about 0.3 wt. %, about 0.32 wt. %, about 0.34 wt. %, about 0.36 wt. %, about 0.38 wt. %, about 0.4 wt. %, about 0.42 wt. %, about 0.44 wt. %, about 0.46 wt. %, about 0.48 wt. %, about 0.50 wt. %, about 0.52 wt. %, about 0.54 wt. %, about 0.56 wt. %, about 0.58 wt. %, about 0.6 wt. %, about 0.62 wt. %, about 0.64 wt. %, about 0.66 wt. %, about 0.68 wt. %, about 0.7 wt. %, about 0.72 wt. %, about 0.74 wt. %, about 0.76 wt. %, about 0.78 wt. %, about 0.8 wt. %, about 0.82 wt. %, about 0.84 wt. %, about 0.86 wt. %, about 0.88 wt. %, about 0.9 wt. %, about 0.92 wt. %, about 0.94 wt. %, about 0.96 wt. %, about 0.98 wt. %, about 1 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, about 1.5 wt. %, about 1.55 wt. %, about 1.6 wt. %, about 1.65 wt. %, about 1.7 wt. %, about 1.75 wt. %, about 1.8 wt. %, about 1.85 wt. %, about 1.9 wt. %, about 1.95 wt. %, about 2 wt. %, about 2.05 wt. %, about 2.1 wt. %, about 2.15 wt. %, about 2.2 wt. %, about 2.25 wt. %, about 2.3 wt. %, about 2.35 wt. %, about 2.4 wt. %, about 2.45 wt. %, about 2.5 wt. %, about 2.55 wt. %, about 2.6 wt. %, about 2.65 wt. %, about 2.7 wt. %, about 2.75 wt. %, about 2.8 wt. %, about 2.85 wt. %, about 2.9 wt. %, about 2.95 wt. %, about 3 wt. %, or any range including and/or in between any two of the preceding values. Additionally or alternatively, in some embodiments, the silver compound comprises one or more pharmaceutically acceptable salts. Additionally or alternatively, in some embodiments, the one or more pharmaceutically acceptable silver salts is selected from the group consisting of silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, silver p-aminosalicylate, nanocrystalline silver, and any combination thereof.

Additionally or alternatively, in some embodiments, each of the first layer and the second layer independently comprises one or more additional biomaterials. Examples of the one or more additional biomaterials include, but are not limited to, gelatin, chitosan, fibronectin, hyaluronic acid, polysaccharides, and any combination thereof.

Additionally or alternatively, in some embodiments, each of the first layer and the second layer independently comprises at least one plasticizer. Additionally or alternatively, in some embodiments, the at least one plasticizer independently comprises about 1 wt. % to about 10 wt. %, or about 1 wt. % to about 15 wt. % of each of the first layer and of the second layer. Additionally or alternatively, in some embodiments, the at least one plasticizer is selected from the group consisting of an acetylated monoglyceride, an alkyl citrate, methyl ricinoleate, glycerol, and any combination thereof. Additionally or alternatively, in some embodiments, the alkyl citrate is triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, or any combination thereof.

Additionally or alternatively, in some embodiments, the solid content of the first layer comprises about 0.1 wt. % to about 5 wt. %, or about 2 wt. % to about 5 wt. %. Additionally or alternatively, in some embodiments, the solid content of the first layer may comprise about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.20 wt. %, about 0.22 wt. %, about 0.24 wt. %, about 0.26 wt. %, about 0.28 wt. %, about 0.30 wt. %, about 0.32 wt. %, about 0.34 wt. %, about 0.36 wt. %, about 0.38 wt. %, about 0.40 wt. %, about 0.42 wt. %, about 0.44 wt. %, about 0.46 wt. %, about 0.48 wt. %, about 0.50 wt. %, about 0.55 wt. %, about 0.60 wt. %, about 0.65 wt. %, about 0.70 wt. %, about 0.75 wt. %, about 0.80 wt. %, about 0.85 wt. %, about 0.90 wt. %, about 0.95 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3.0 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4.0 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5.0 wt. %, or any range including and/or in between any two of the preceding values.

Additionally or alternatively, in some embodiments, the solid content of the second layer comprises about 2 wt. % to about 10 wt. %, or about 4 wt. % to about 10 wt. %. Additionally or alternatively, in some embodiments, the solid content of the second layer may comprise about 2.0 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3.0 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4.0 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5.0 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6.0 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7.0 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8.0 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9.0 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, or any range including and/or in between any two of the preceding values.

Additionally or alternatively, in some embodiments, each of the first layer and the second layer independently comprise a wound-facing side and an environmental-facing side, and wherein the wound-facing side of the second layer is coupled with the environmental-facing side of the first layer.

Additionally or alternatively, in some embodiments, the wound dressing composition further comprises a third layer and a fourth layer, wherein each of the third layer and the fourth layer independently comprises a homogeneous mixture of a collagen, an oxidized cellulose, and a silver compound.

Additionally or alternatively, in some embodiments, each of the third layer and the fourth layer independently comprise a wound-facing side and an environmental-facing side.

Additionally or alternatively, in some embodiments, the oxidized cellulose of the third layer and the fourth layer independently comprises oxidized regenerated cellulose (ORC). Additionally or alternatively, in some embodiments, the third layer and the fourth layer each independently comprises about 30 wt. % to about 70 wt. % of the oxidized cellulose, with a weight-average molecular weight of about 10,000 to about 1,000,000. Additionally or alternatively, in some embodiments, the oxidized cellulose of each of the third layer and the fourth layer may independently comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, or any range including and/or in between any two of the preceding values. Additionally or alternatively, in some embodiments, the oxidized cellulose of each of the third layer and the fourth layer may independently comprise a weight-average molecular weight of about 10,000, about 11,000, about 12,000, about 13,000, about 14,000, about 15,000, about 16,000, about 17,000, about 18,000, about 19,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 55,000, about 60,000, about 65,000, about 70,000, about 75,000, about 80,000, about 85,000, about 90,000, about 95,000, about 100,000, about 110,000, about 120,000, about 130,000, about 140,000, about 150,000, about 160,000, about 170,000, about 180,000, about 190,000, about 200,000, about 210,000, about 220,000, about 230,000, about 240,000, about 250,000, about 260,000, about 270,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 460,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, or any range including and/or in between any two of the preceding values.

Additionally or alternatively, in some embodiments, the oxidized cellulose of each of the third layer and the fourth layer independently comprises fiber lengths of about 5 μm to about 1,000 μm. Additionally or alternatively, in some embodiments, the oxidized cellulose of each of the third layer and the fourth layer may independently comprise fibers lengths of about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 22 μm, about 24 μm, about 26 μm, about 28 μm, about 30 μm, about 32 μm, about 34 μm, about 36 μm, about 38 μm, about 40 μm, about 42 μm, about 44 μm, about 46 μm, about 48 μm, about 50 μm, about 55 μm, about 60 μm, about 65 μm, about 70 μm, about 75 μm, about 80 μm, about 85 μm, about 90 μm, about 95 μm, about 100 μm, about 110 μm, about 120 μm, about 130 μm, about 140 μm, about 150 μm, about 160 μm, about 170 μm, about 180 μm, about 190 μm, about 200 μm, about 220 μm, about 230 μm, about 240 μm, about 250 μm, about 260 μm, about 280 μm, about 300 μm, about 320 μm, about 340 μm, about 360 μm, about 380 μm, about 400 μm, about 420 μm, about 440 μm, about 460 μm, about 480 μm, about 500 μm, about 550 μm, about 600 μm, about 650 μm, about 700 μm, about 750 μm, about 800 μm, about 850 μm, about 900 μm, about 950 μm, about 1,000 μm, or any range including and/or in between any two of the preceding values.

Additionally or alternatively, in some embodiments, the collagen of each of the third layer and the fourth layer is independently a mammalian collagen. Additionally or alternatively, in some embodiments, the mammalian collagen is selected from the group consisting of a bovine collagen, a human collagen, a recombinantly derived collagen, and any combination thereof. Additionally or alternatively, in some embodiments, each of the third layer and the fourth layer independently comprises about 0.1 wt. % to about 60 wt. %, or about 30 wt. % to about 95 wt. % of the mammalian collagen, with a weight-average molecular weight of about 5,000 to about 100,000. Additionally or alternatively, in some embodiments, the mammalian collagen of each of the third layer and the fourth layer independently comprises a weight-average molecular weight of about 5,000, about 6,000, about 7,000, about 8,000, about 9,000, about 10,000, about 12,000, about 14,000, about 16,000, about 18,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 52,000, about 54,000, about 56,000, about 58,000, about 60,000, about 62,000, about 64,000, about 66,000, about 68,000, about 70,000, about 72,000, about 74,000, about 76,000, about 78,000, about 80,000, about 82,000, about 84,000, about 86,000, about 88,000, about 90,000, about 92,000, about 94,000, about 96,000, about 98,000, about 100,000, or any range including and/or in between any two of the preceding values.

Additionally or alternatively, in some embodiments, each of the third layer and the fourth layer may independently comprise a ratio of collagen to ORC of about 60:40 to about 40:60. Additionally or alternatively, in some embodiments, each of the third layer and the fourth layer may independently comprise a ratio of collagen to ORC of about 60:40, about 55:45, about 50:50, about 45:55, about 40:60, or any range including and/or in between any two of the preceding values.

Additionally or alternatively, in some embodiments, each of the third layer and the fourth layer independently comprises about 0.1 wt. % to about 1 wt. %, or about 0.1 wt. % to about 3 wt. % of the silver compound. Additionally or alternatively, in some embodiments, the silver compound of each of the third layer and the fourth layer may independently comprise about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.22 wt. %, about 0.24 wt. %, about 0.26 wt. %, about 0.28 wt. %, about 0.3 wt. %, about 0.32 wt. %, about 0.34 wt. %, about 0.36 wt. %, about 0.38 wt. %, about 0.4 wt. %, about 0.42 wt. %, about 0.44 wt. %, about 0.46 wt. %, about 0.48 wt. %, about 0.50 wt. %, about 0.52 wt. %, about 0.54 wt. %, about 0.56 wt. %, about 0.58 wt. %, about 0.6 wt. %, about 0.62 wt. %, about 0.64 wt. %, about 0.66 wt. %, about 0.68 wt. %, about 0.7 wt. %, about 0.72 wt. %, about 0.74 wt. %, about 0.76 wt. %, about 0.78 wt. %, about 0.8 wt. %, about 0.82 wt. %, about 0.84 wt. %, about 0.86 wt. %, about 0.88 wt. %, about 0.9 wt. %, about 0.92 wt. %, about 0.94 wt. %, about 0.96 wt. %, about 0.98 wt. %, about 1 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, about 1.5 wt. %, about 1.55 wt. %, about 1.6 wt. %, about 1.65 wt. %, about 1.7 wt. %, about 1.75 wt. %, about 1.8 wt. %, about 1.85 wt. %, about 1.9 wt. %, about 1.95 wt. %, about 2 wt. %, about 2.05 wt. %, about 2.1 wt. %, about 2.15 wt. %, about 2.2 wt. %, about 2.25 wt. %, about 2.3 wt. %, about 2.35 wt. %, about 2.4 wt. %, about 2.45 wt. %, about 2.5 wt. %, about 2.55 wt. %, about 2.6 wt. %, about 2.65 wt. %, about 2.7 wt. %, about 2.75 wt. %, about 2.8 wt. %, about 2.85 wt. %, about 2.9 wt. %, about 2.95 wt. %, about 3 wt. %, or any range including and/or in between any two of the preceding values. Additionally or alternatively, in some embodiments, the silver compound comprises one or more pharmaceutically acceptable salts. Additionally or alternatively, in some embodiments, the one or more pharmaceutically acceptable silver salts is selected from the group consisting of silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, silver p-aminosalicylate, nanocrystalline silver, and any combination thereof.

Additionally or alternatively, in some embodiments, each of the third layer and the fourth layer independently comprises one or more additional biomaterials. Examples of the one or more additional biomaterials include, but are not limited to, gelatin, chitosan, fibronectin, hyaluronic acid, polysaccharides, and any combination thereof.

Additionally or alternatively, in some embodiments, each of the third layer and the fourth layer independently comprises at least one plasticizer. Additionally or alternatively, in some embodiments, the at least one plasticizer independently comprises about 1 wt. % to about 10 wt. %, or about 1 wt. % to about 15 wt. % of each of the third layer and the fourth layer. Additionally or alternatively, in some embodiments, the at least one plasticizer is selected from the group consisting of an acetylated monoglyceride, an alkyl citrate, methyl ricinoleate, glycerol, and any combination thereof. Additionally or alternatively, in some embodiments, the alkyl citrate is triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, or any combination thereof.

Additionally or alternatively, in some embodiments, the solid content of each of the third layer and the fourth layer independently comprises about 0.1 wt. % to about 10 wt. %. Additionally or alternatively, in some embodiments, the solid content of the second layer may comprise about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.20 wt. %, about 0.22 wt. %, about 0.24 wt. %, about 0.26 wt. %, about 0.28 wt. %, about 0.30 wt. %, about 0.32 wt. %, about 0.34 wt. %, about 0.36 wt. %, about 0.38 wt. %, about 0.40 wt. %, about 0.42 wt. %, about 0.44 wt. %, about 0.46 wt. %, about 0.48 wt. %, about 0.50 wt. %, about 0.55 wt. %, about 0.60 wt. %, about 0.65 wt. %, about 0.70 wt. %, about 0.75 wt. %, about 0.80 wt. %, about 0.85 wt. %, about 0.90 wt. %, about 0.95 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3.0 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4.0 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5.0 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6.0 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7.0 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8.0 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9.0 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, or any range including and/or in between any two of the preceding values.

Additionally or alternatively, in some embodiments, each of the first layer, the second layer, and the third layer independently comprise a wound-facing side and an environmental-facing side, and wherein the wound-facing side of the third layer is coupled with the environmental-facing side of the second layer, and wherein the wound-facing side of the second layer is coupled with the environmental-facing side of the first layer.

Additionally or alternatively, in some embodiments, each of the first layer, the second layer, the third layer, and the fourth layer independently comprise a wound-facing side and an environmental-facing side, and wherein the wound-facing side of the fourth layer is coupled with the environmental-facing side of the third layer, the wound-facing side of the third layer is coupled with the environmental-facing side of the second layer, and wherein the wound-facing side of the second layer is coupled with the environmental-facing side of the first layer.

Additionally or alternatively, in some embodiments, the wound dressing composition is capable of preventing, reducing, inhibiting, or disrupting biofilm formation in a wound.

Additionally or alternatively, in some embodiments, the wound dressing composition is capable of reducing biofilm formation by about $\geq 2$ $\log_{10}$ units after 12 hours in vitro exposure, or about $\geq 3$ $\log_{10}$ units after 24 hours. Additionally or alternatively, in some embodiments, the wound dressing composition is capable of maintaining reduced biofilm levels by about $\geq 2$ $\log_{10}$ units after 12 hours in vitro exposure, or about $\geq 3$ $\log_{10}$ units after 24 hours.

Additionally or alternatively, in some embodiments, the wound dressing composition is capable of reducing a biofilm by about 10% to about 100% after 24 hours in vitro exposure.

Additionally or alternatively, in some embodiments, the wound dressing composition exhibits about 10% to about 100% reduction in tackiness observed compared to that observed with a control wound dressing prepared with water. Additionally or alternatively, in some embodiments, the wound dressing composition exhibits about 10%, about 11%, about 12%, about 13%, about 14%, about 15%, about 16%, about 17%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, about 100%, or any range including and/or in between any two of the preceding values, reduction in tackiness observed compared to that observed with a control wound dressing prepared with water.

In another aspect, the present disclosure provides a method for treating a wound in a subject in need thereof, comprising administering to the wound a wound dressing composition of any embodiment disclosed herein. Additionally or alternatively, in some embodiments, the wound comprises a biofilm and the wound dressing composition prevents, reduces, inhibits, or disrupts the biofilm. Additionally or alternatively, in some embodiments, the wound dressing composition is bioresorbable. Additionally or alternatively, in some embodiments, the wound dressing composition is administered directly to the wound.

In another aspect, the present disclosure provides a method for making a wound dressing composition comprising, providing a first layer comprising an effective amount of a homogeneous mixture of a collagen, an oxidized cellulose, and at least one bacteria reducing active ingredient, providing a second layer comprising an effective amount of a homogeneous mixture of a collagen, an oxidized cellulose, a silver compound, and at least one bacteria reducing active ingredient, and combining the first layer and the second layer to form the wound dressing composition. Additionally or alternatively, in some embodiments, the at least one bacteria reducing active ingredient of each of the first layer and of the second layer is mixed with a solvent, wherein the solvent is water, a ($C_1$-$C_3$) alcohol or an aqueous solution thereof. Additionally or alternatively, in some embodiments, the ($C_1$-$C_3$)alcohol comprises one or more of methanol, ethanol, propanol, isopropanol, or any combination thereof.

Also provided herein are kits comprising the wound dressing compositions of any embodiment described herein and instructions for use.

DETAILED DESCRIPTION

It is to be appreciated that certain aspects, modes, embodiments, variations and features of the present methods are described below in various levels of detail in order to provide a substantial understanding of the present technology.

Wounds are typically contaminated by bacteria, however when the immune system cannot cope with normal bacterial growth, a wound can become infected. An infected wound is a wound in which bacteria or other microorganisms have colonized, causing a deterioration and delay in the healing of the wound. Thus, a reduction in bacterial colonization is vital in wound therapy.

A biofilm comprises a polysaccharide extracellular matrix produced by an association of microorganisms (e.g., single or multiple species) that have adhered onto a surface. These three-dimensional microbial communities can have coordinated multi-cellular behavior, thereby forming an extracellular matrix in which the bacteria are embedded. The ability of bacteria to form these complex biofilms can impede a host's defense mechanisms against pathogens. As such, biofilms often display a heightened tolerance to antimicrobial treatment. The present disclosure provides wound dressing compositions that include a biofilm disrupting, bacteria reducing active ingredient and an antimicrobial silver compound. Example 2 of the present disclosure demonstrates that the wound dressing compositions of the present technology will be useful for treating infected wounds and/or wounds comprising a biofilm. High concentrations of silver products used in a wound-interface layer have been reported to stain the skin in and around the wound due to high concentrations of silver being released at the wound surface, which may also delay epithelialization. Some have also observed the absorption of silver, systemic distribution of silver and excretion of silver in urine among patients who have used topical silver products. See Karlock, L. *Podiatry Today*, 17:32-35 (2004). Thus, the wound dressings of the present technology advantageously contain an antimicrobial silver compound in the second layer of the wound dressing, thereby mitigating concerns with silver-toxicity while simultaneously being effective at treating infected wounds and/or wounds comprising a biofilm.

Definitions

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, $C_m$-$C_n$, such as $C_1$-$C_{12}$, $C_1$-$C_6$, or $C_1$-$C_3$ when used before a group refers to that group containing m to n carbon atoms.

As used herein, "homogeneous" will be understood by persons of ordinary skill in the art to refer to a solid, a liquid, or a gas mixture that has uniform proportions and/or distributions of its components throughout any given sample.

As used herein, the term "solid content" refers to the density of a layer of the wound dressing composition of the present technology, which is its mass per unit volume.

The term "mammalian recombinant collagen" refers to collagen manufactured by culturing a non-human organism or mammalian or non-mammalian cells to express at least one exogenous gene encoding a collagen in the culturing system. The collagen may be recombinantly manufactured by a plant (e.g., CollPlant, CollPlant Holdings Ltd., Ness Ziona, Israel) such as tobacco, or in yeast. The term "human recombinant collagen" refers to collagen manufactured by culturing a non-human organism or mammalian or non-mammalian cells to express at least one human gene encoding a collagen. The human recombinant collagen may be selected from the group consisting of collagen type I, type II, type III, type IV, type V, type VI, type VII, type VIII, type IX, type X, type XI, type XII, type XIII, type XIV, type XV, type XVI, type XVII, type XVIII, type XIX, type XX, type XXI, type XXII, type XXIII, type XXIV, type XXV, type XXVI, and type XXVII. The human recombinant collagen can be collagen of one type free of any other type, or can be a mixture of collagen types. Suitably, the human recombinant collagen comprises collagens selected from the group consisting of collagen type I, collagen type III, and mixtures thereof. The term "bovine recombinant collagen" refers to collagen manufactured by culturing a non-human organism or mammalian or non-mammalian cells to express at least one bovine gene encoding a collagen. The bovine recombinant collagen may be selected from the group consisting of collagen type I, type II, type III, and type IV. The bovine recombinant collagen can be collagen of one type free of any other type, or can be a mixture of collagen types. Suitably, the bovine recombinant collagen comprises collagens selected from the group consisting of collagen type I, collagen type III, and mixtures thereof.

As used herein, the term "biofilm" refers to an extracellular matrix created by an association of microorganisms, e.g., single or multiple species. The microorganisms can be encased or embedded in a matrix material, which may be self-produced by resident microorganisms. The biofilm may be present or adhere to living and/or non-living surfaces, e.g., tissue, a wound, medical implants, including but not limited to, orthopedic implants, dental implants, catheters, stents and so on. Exemplary microorganisms include, but are not limited to bacteria, e.g., Gram-negative bacteria, such as *Pseudomonas aeruginosa*, Gram-positive bacteria, such as

*Staphylococcus aureus* and *Streptococcus mutans*, and fungi, such as yeasts, e.g., *Candida albicans*. The term "matrix material" is intended to encompass extracellular polymeric substances. Exemplary matrix materials include, but are not limited to polysaccharides, glycoproteins and/or nucleic acids. The term "biofilm" is further intended to include biological films that develop and persist at interfaces in aqueous environments. The language "biofilm development" or "biofilm formation" is intended to include the formation, growth, and modification of the bacterial colonies contained with biofilm structures, as well as the synthesis and maintenance of the exopolysaccharide of the biofilm structures. "Reducing" or "disrupting" a biofilm includes reducing the number of total viable microorganisms making up and/or embedded in at least part of the biofilm, for example, as measured by total viable counts (TVC) of microorganisms (e.g., bacteria, yeast).

As understood by one of ordinary skill in the art, "weight-average molecular weight" (also known as "relative molar mass") is a dimensionless quantity but is converted to molar mass by multiplying by 1 gram/mole—for example, collagen with a weight-average molecular weight of 5,000 has a weight-average molar mass of 5,000 g/mol.

As used herein, pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

As used herein, the "administration" of a wound dressing composition to a subject includes any route of introducing or delivering to a subject a wound dressing composition to perform its intended function. Administration can be carried out by any suitable route, including but not limited to, topical administration. Administration includes self-administration and the administration by another.

As used herein, the term "effective amount" refers to a quantity sufficient to achieve a desired therapeutic and/or prophylactic effect, e.g., an amount which results in the decrease in biofilm formation in a wound described herein or one or more signs or symptoms associated with delayed wound healing described herein. In the context of therapeutic or prophylactic applications, the amount of a composition administered to the subject will vary depending on the composition, the degree, type, and severity of the wound and on the characteristics of the individual. The compositions can also be administered in combination with one or more additional therapeutic compounds. In the methods described herein, the therapeutic compositions may be administered to a subject having one or more wounds.

As used herein, the terms "individual", "patient", or "subject" can be an individual organism, a vertebrate, a mammal, or a human. In some embodiments, the individual, patient or subject is a human.

"Treating" or "treatment" as used herein covers the treatment of a wound described herein, in a subject, such as a human, and includes: (i) inhibiting a wound, i.e., arresting its development; (ii) relieving a wound, i.e., causing regression of the wound; (iii) slowing progression of the wound; and/or (iv) inhibiting, relieving, or slowing progression of one or more symptoms of the wound. In some embodiments, treatment means that the symptoms associated with the wound are, e.g., alleviated, reduced, cured, or placed in a state of remission.

It is also to be appreciated that the various modes of treatment of wounds as described herein are intended to mean "substantial," which includes total but also less than total treatment, and wherein some biologically or medically relevant result is achieved. The treatment may be a continuous prolonged treatment for a chronic wound or a single, or few time administrations for the treatment of an acute wound.

The Wound Dressing of the Present Technology

The First Layer

The present disclosure provides a wound dressing composition comprising a first layer wherein the first layer comprises a homogeneous mixture of a collagen, an oxidized cellulose, and at least one bacteria reducing active ingredient.

In any embodiment disclosed herein, the first layer comprises a wound-facing side and an environmental-facing side.

In any embodiment disclosed herein, the collagen of the first layer may comprise mammalian collagen. Additionally or alternatively, in some embodiments, the collagen of the first layer may comprise a human collagen. Additionally or alternatively, in some embodiments, the human collagen may comprise human collagen type I and human collagen type III. Additionally or alternatively, in some embodiments, the collagen of the first layer may comprise a bovine collagen. Additionally or alternatively, in some embodiments, the collagen of the first layer may comprise bovine collagen type I, bovine collagen type II, bovine collagen type III, and bovine collagen type IV. Additionally or alternatively, in some embodiments, the collagen of the first layer may comprise bovine collagen type I and bovine collagen type III.

In any embodiment disclosed herein, the collagen of the first layer may be provided by any manner known in the art. Additionally or alternatively, in some embodiments, the collagen may be provided by a tissue sample or recombinantly manufactured. Additionally or alternatively, in some embodiments, mammalian recombinant collagen of the first layer may be provided by any suitable method known in the art. Additionally or alternatively, in some embodiments, human recombinant collagen of the first layer may be provided by any suitable method known in the art. For example, the step of providing human recombinant collagen may comprise following the protocol described in U.S. Pat. No. 5,962,648, the entire content of which is incorporated herein by reference. Further recombinant processes are set forth in U.S. Pat. No. 5,593,859 and WO2004/078120, which are also incorporated herein by reference. Additionally or alternatively, in some embodiments, collagen will be recombinantly manufactured by culturing a cell which has been transfected with at least one gene encoding a polypeptide comprising collagen and genes encoding oxidized cellulose and subunits of the post-translational enzyme prolyl 4-hydroxylase, and purifying the resultant collagen monomer therefrom. Additionally or alternatively, in some embodiments, collagen will be recombinantly manufactured by a plant (e.g., CollPlant, CollPlant Holdings Ltd., Ness Ziona, Israel) such as tobacco, or in yeast. The human recombinant collagen solution may be subsequently subjected to polymerization or cross-linking conditions to produce an insoluble fibrous collagen.

In any embodiment disclosed herein, the collagen may be a type I collagen, a type II collagen, or a type III collagen. Additionally or alternatively, in some embodiments, the collagen may be obtained from any natural source, may be chemically-modified collagen (e.g., an atelocollagen obtained by removing the immunogenic telopeptides from natural collagen), or may be any combination thereof. For example, the collagen may include collagen obtained from bovine corium that has been rendered largely free of non-collagenous components, for example, including fat, non-collagenous proteins, polysaccharides, and other carbohydrates, such as by procedures described in U.S. Pat. Nos. 4,614,794 and 4,320,201, the entire contents of which are incorporated by reference.

In any embodiment disclosed herein, the collagen of the first layer may comprise about 0.1 wt. % to about 60 wt. %, or about 30 wt. % to about 95 wt. %, with a weight-average molecular weight of about 5,000 to about 100,000. Additionally or alternatively, in some embodiments, the amount of collagen in the first layer may be about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.2 wt. %, about 2.4 wt. %, about 2.6 wt. %, about 2.8 wt. %, about 3 wt. %, about 3.2 wt. %, about 3.4 wt. %, about 3.6 wt. %, about 3.8 wt. %, about 4 wt. %, about 4.2 wt. %, about 4.4 wt. %, about 4.6 wt. %, about 4.8 wt. %, about 5 wt. %, about 5.2 wt. %, about 5.4 wt. %, about 5.6 wt. %, about 5.8 wt. %, about 6 wt. %, about 6.2 wt. %, about 6.4 wt. %, about 6.6 wt. %, about 6.8 wt. %, about 7 wt. %, about 7.2 wt. %, about 7.4 wt. %, about 7.6 wt. %, about 7.8 wt. %, about 8 wt. %, about 8.2 wt. %, about 8.4 wt. %, about 8.6 wt. %, about 8.8 wt. %, about 9 wt. %, about 9.2 wt. %, about 9.4 wt. %, about 9.6 wt. %, about 9.8 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, about 92 wt. %, about 94 wt. %, about 95 wt. %, or any range including and/or in between any two of the preceding values. Additionally or alternatively, in some embodiments, the collagen of the first layer comprises a weight-average molecular weight of about 5,000, about 6,000, about 7,000, about 8,000, about 9,000, about 10,000, about 12,000, about 14,000, about 16,000, about 18,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 52,000, about 54,000, about 56,000, about 58,000, about 60,000, about 62,000, about 64,000, about 66,000, about 68,000, about 70,000, about 72,000, about 74,000, about 76,000, about 78,000, about 80,000, about 82,000, about 84,000, about 86,000, about 88,000, about 90,000, about 92,000, about 94,000, about 96,000, about 98,000, about 100,000, or any range including and/or in between any two of the preceding values.

In any embodiment disclosed herein, the collagen of the first layer may comprise a weight ratio of human collagen type I to human collagen type III of about 100:0, about 90:10, about 80:20, about 70:30, about 60:40, about 50:50, about 40:60, about 30:70, about 20:80, about 10:90, about 0:100, or any range including and/or in between any two of the preceding values. Additionally or alternatively, in some embodiments, the ratio by weight of human collagen type I to human collagen type III is greater than about 50:50, or greater than about 70:30. Additionally or alternatively, in some embodiments, the collagen of the first layer may comprise a weight ratio of type I bovine collagen to type III bovine collagen of about 85:15.

Additionally or alternatively, in some embodiments, the oxidized cellulose of the first layer comprises oxidized regenerated cellulose (ORC). In any embodiment disclosed herein, ORC may be produced by the oxidation of cellulose, for example with dinitrogen tetroxide and/or as described in U.S. Pat. No. 3,122,479 (incorporated herein by reference). Without wishing to be bound by theory, it is believed that this process may convert primary alcohol groups on the saccharide residues of the celluolse to carboxylic acid groups, for example, forming uronic acid residues within the cellulose chain. The oxidation need not proceed with complete selectivity, and as a result hydroxyl groups on carbons 2 and 3 of the saccharide residue may be converted to the keto form. These ketone units may introduce an alkali labile link, which at pH 7 or higher initiates the decomposition of the polymer via formation of a lactone and sugar ring cleavage. As a result, oxidized regenerated cellulose is biodegradable and bioresorbable under physiological conditions. ORC is available with a variety of degrees of oxidation and hence rates of degradation.

In any embodiment disclosed herein, the ORC of the first layer may comprise about 30 wt. % to about 70 wt. %, with a weight-average molecular weight of about 10,000 to about 1,000,000. Additionally or alternatively, in some embodiments, the ORC in the first layer may comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, or any range including and/or in between any two of the preceding values. Additionally or alternatively, in some embodiments, the ORC of the first layer may comprise a weight-average molecular weight of about 10,000, about 11,000, about 12,000, about 13,000, about 14,000, about 15,000, about 16,000, about 17,000, about 18,000, about 19,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 55,000, about 60,000, about 65,000, about 70,000, about 75,000, about 80,000, about 85,000, about 90,000, about 95,000, about 100,000, about 110,000, about 120,000, about 130,000, about 140,000, about 150,000, about 160,000, about 170,000, about 180,000, about 190,000, about 200,000, about 210,000, about 220,000, about 230,000, about 240,000, about 250,000, about 260,000, about 270,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 460,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, or any range including and/or in between any two of the preceding values.

The ORC may include particles, fibers, or both; in any embodiment disclosed herein, the ORC may be in the form of particles, such as fiber particles or powder particles. In embodiments that include ORC fibers, the ORC fibers may have a volume fraction such that at least 80% of the fibers have lengths in the range from about 5 µm to about 1,000 µm. Additionally or alternatively, in some embodiments, the ORC of the first layer may comprise fibers lengths of about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 22 µm, about 24 µm, about 26 µm, about 28 µm, about 30 µm, about 32 µm, about 34 µm, about 36 µm, about 38 µm, about 40 µm, about 42 µm, about 44 µm, about 46 µm, about 48 µm, about 50 µm, about 55 µm, about 60 µm, about 65 µm, about 70 µm, about 75 µm, about 80 µm, about 85 µm, about 90 µm, about 95 µm, about 100 µm, about 110 µm, about 120 µm, about 130 µm, about 140 µm, about 150 µm, about 160 µm, about 170 µm, about 180 µm, about 190 µm, about 200 µm, about 220 µm, about 230 µm, about 240 µm, about 250 µm, about 260 µm, about 280 µm, about 300 µm, about 320 µm, about 340 µm, about 360 µm, about 380 µm, about 400 µm, about 420 µm, about 440 µm, about 460 µm, about 480 µm, about 500 µm, about 550 µm, about 600 µm, about 650 µm, about 700 µm, about 750 µm, about 800 µm, about 850 µm, about 900 µm, about 950 µm, about 1,000 µm, or any range including and/or in between any two of the preceding values.

In any embodiment disclosed herein, the mixture of collagen and ORC within the first layer of the present technology may comprise about 30 wt. % to about 90 wt. %. Additionally or alternatively, in some embodiments, the collagen and ORC mixture of the first layer may comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, or any range including and/or in between any two of the preceding values.

In any embodiment disclosed herein, the mixture of collagen and ORC within the first layer of the present technology may comprise a ratio of about 90:10 to 10:90, or about 60:40 to about 40:60. Additionally or alternatively, in some embodiments, the mixture of collagen and ORC within the first layer may comprise a ratio of about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, or any range including and/or in between any two of the preceding values.

In any embodiment disclosed herein, the bacteria reducing active ingredient of the first layer may comprise an organic acid or a pharmaceutically acceptable salt thereof. Additionally or alternatively, in some embodiments, the bacteria reducing active ingredient of the first layer may be selected from the group consisting of citric acid, acetic acid, or any pharmaceutically acceptable salt thereof, and any combination thereof. Additionally or alternatively, in some embodiments, the bacteria reducing active ingredient of the first layer may be present in a concentration of about 50 mM to about 400 mM. Additionally or alternatively, in some embodiments, the bacteria reducing active ingredient of the first layer may be present in a concentration of about 50 mM, about 52 mM, about 54 mM, about 56 mM, about 58 mM, about 60 mM, about 62 mM, about 64 mM, about 66 mM, about 68 mM, about 70 mM, about 72 mM, about 74 mM, about 76 mM, about 78 mM, about 80 mM, about 82 mM, about 84 mM, about 86 mM, about 88 mM, about 90 mM, about 92 mM, about 94 mM, about 96 mM, about 98 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, or any range including and/or in between any two of the preceding values. Additionally or alternatively, in some embodiments, the bacteria reducing active ingredient of the first layer may be present in a concentration of about 100 mM to about 250 mM.

In any embodiment disclosed herein, the at least one bacteria reducing active ingredient of the first layer may be mixed with a solvent, wherein the solvent is water, a $(C_1-C_3)$alcohol or an aqueous solution thereof. Additionally or alternatively, in some embodiments, the $(C_1-C_3)$alcohol may be one or more of methanol, ethanol, propanol, isopropanol, or any combination thereof.

In any embodiment disclosed herein, the first layer may comprise about 1 wt. % to about 25 wt. % of one or more additional biomaterials. Additionally or alternatively, in some embodiments, the one or more additional biomaterials of the first layer may comprise about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, or any range including and/or in between any two of the preceding values. Additionally or alternatively, in some embodiments, the one or more additional biomaterials included in the first layer may be selected from the group consisting of gelatin, chitosan, fibronectin, hyaluronic acid, polysaccharides, and any combination thereof.

In any embodiment disclosed herein, the first layer may comprise about 1 wt. % to about 10 wt. %, or about 1 wt. % to about 15 wt. % of at least one plasticizer. Additionally or alternatively, in some embodiments, the at least one plasticizer of the first layer may comprise about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.2 wt. %, about 2.4 wt. %, about 2.6 wt. %, about 2.8 wt. %, about 3 wt. %, about 3.2 wt. %, about 3.4 wt. %, about 3.6 wt. %, about 3.8 wt. %, about 4 wt. %, about 4.2 wt. %, about 4.4 wt. %, about 4.6 wt. %, about 4.8 wt. %, about 5 wt. %, about 5.2 wt. %, about 5.4 wt. %, about 5.6 wt. %, about 5.8 wt. %, about 6 wt. %, about 6.2 wt. %, about 6.4 wt. %, about 6.6 wt. %, about 6.8 wt. %, about 7 wt. %, about 7.2 wt. %, about 7.4 wt. %, about 7.6 wt. %, about 7.8 wt. %, about 8 wt. %, about 8.2 wt. %, about 8.4 wt. %, about 8.6 wt. %, about 8.8 wt. %, about 9 wt. %, about 9.2 wt. %, about 9.4 wt. %, about 9.6 wt. %, about 9.8 wt. %, about 10 wt. %, about 10.2 wt. %, about 10.4 wt. %, about 10.6 wt. %, about 10.8 wt. %, about 11 wt. %, about 11.2 wt. %, about 11.4 wt. %, about 11.6 wt. %, about 11.8 wt. %, about 12 wt. %, about 12.2 wt. %, about 12.4 wt. %, about 12.6 wt. %, about 12.8 wt. %, about 13 wt. %, about 13.2 wt. %, about 13.4 wt. %, about 13.6 wt. %, about 13.8 wt. %, about 14 wt. %, about 14.2 wt. %, about 14.4 wt. %, about 14.6 wt. %, about 14.8 wt. %, about 15 wt. %, or any range including and/or in between any two of the preceding values. Exemplary plasticizers include, but are not limited to, an acetylated monoglyceride, an alkyl citrate, methyl ricinoleate, glycerol, polyvinylpyrrolidone, and any combination thereof. Examples of alkyl citrates include, but are not limited to, triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, and any combination thereof.

In any embodiment disclosed herein, the solid content of the first layer may comprise about 0.1 wt. % to about 5 wt. %, or about 2 wt. % to about 5 wt. %. Additionally or alternatively, in some embodiments, the solid content of the first layer may comprise about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.22 wt. %, about 0.24 wt. %, about 0.26 wt. %, about 0.28 wt. %, about 0.3 wt. %, about 0.32 wt. %, about 0.34 wt. %, about 0.36 wt. %, about 0.38 wt. %, about 0.4 wt. %, about 0.42 wt. %, about 0.44 wt. %, about 0.46 wt. %, about 0.48 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, or any range including and/or in between any two of the preceding values.

The Second Layer

The present disclosure provides a wound dressing composition comprising a second layer wherein the second layer comprises a homogeneous mixture of a collagen, an oxidized cellulose, a silver compound, and at least one bacteria reducing active ingredient.

In any embodiment disclosed herein, the second layer comprises a wound-facing side and an environmental-facing side.

In any embodiment disclosed herein, the collagen of the second layer may comprise mammalian collagen. Additionally or alternatively, in some embodiments, the collagen of the second layer may comprise a human collagen. Additionally or alternatively, in some embodiments, the human collagen may comprise human collagen type I and human collagen type III. Additionally or alternatively, in some embodiments, the collagen of the second layer may comprise a bovine collagen. Additionally or alternatively, in some embodiments, the collagen of the second layer may comprise bovine collagen type I, bovine collagen type II, bovine collagen type III, and bovine collagen type IV. Additionally or alternatively, in some embodiments, the collagen of the second layer may comprise bovine collagen type I and bovine collagen type III.

In any embodiment disclosed herein, the collagen of the second layer may be provided by any manner known in the art. Additionally or alternatively, in some embodiments, the collagen may be provided by a tissue sample or recombinantly manufactured. Additionally or alternatively, in some embodiments, mammalian recombinant collagen of the second layer may be provided by any suitable method known in the art. Additionally or alternatively, in some embodiments, human recombinant collagen of the second layer may be provided by any suitable method known in the art. For example, the step of providing human recombinant collagen may comprise following the protocol described in U.S. Pat. No. 5,962,648, the entire content of which is incorporated herein by reference. Further recombinant processes are set forth in U.S. Pat. No. 5,593,859 and WO2004/078120, which are also incorporated herein by reference. Additionally or alternatively, in some embodiments, collagen will be recombinantly manufactured by culturing a cell which has been transfected with at least one gene encoding a polypeptide comprising collagen and genes encoding oxidized cellulose and subunits of the post-translational enzyme prolyl 4-hydroxylase, and purifying the resultant collagen monomer therefrom. Additionally or alternatively, in some embodiments, collagen will be recombinantly manufactured by a plant (e.g., CollPlant, CollPlant Holdings Ltd., Ness Ziona, Israel) such as tobacco, or in yeast. The human recombinant collagen solution may be subsequently subjected to polymerization or cross-linking conditions to produce an insoluble fibrous collagen.

In any embodiment disclosed herein, the collagen may be a type I collagen, a type II collagen, or a type III collagen. Additionally or alternatively, in some embodiments, the collagen may be obtained from any natural source, may be chemically-modified collagen (e.g., an atelocollagen obtained by removing the immunogenic telopeptides from natural collagen), or may be any combination thereof. For example, the collagen may include collagen obtained from bovine corium that has been rendered largely free of non-collagenous components, for example, including fat, non-collagenous proteins, polysaccharides, and other carbohydrates, such as by procedures described in U.S. Pat. Nos. 4,614,794 and 4,320,201, the entire contents of which are incorporated by reference.

In any embodiment disclosed herein, the collagen of the second layer may comprise about 0.1 wt. % to about 60 wt. %, or about 30 wt. % to about 95 wt. %, with a weight-average molecular weight of about 5,000 to about 100,000. Additionally or alternatively, in some embodiments, the amount of collagen in the second layer may be about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.2 wt. %, about 2.4 wt. %, about 2.6 wt. %, about 2.8 wt. %, about 3 wt. %, about 3.2 wt. %, about 3.4 wt. %, about 3.6 wt. %, about 3.8 wt. %, about 4 wt. %, about 4.2 wt. %, about 4.4 wt. %, about 4.6 wt. %, about 4.8 wt. %, about 5 wt. %, about 5.2 wt. %, about 5.4 wt. %, about 5.6 wt. %, about 5.8 wt. %, about 6 wt. %, about 6.2 wt. %, about 6.4 wt. %, about 6.6 wt. %, about 6.8 wt. %, about 7 wt. %, about 7.2 wt. %, about 7.4 wt. %, about 7.6 wt. %, about 7.8 wt. %, about 8 wt. %, about 8.2 wt. %, about 8.4 wt. %, about 8.6 wt. %, about 8.8 wt. %, about 9 wt. %, about 9.2 wt. %, about 9.4 wt. %, about 9.6 wt. %, about 9.8 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, about 92 wt. %, about 94 wt. %, about 95 wt. %, or any range including and/or in between any two of the preceding values. Additionally or alternatively, in some embodiments, the collagen of the second layer comprises a weight-average molecular weight of about 5,000, about 6,000, about 7,000, about 8,000, about 9,000, about 10,000, about 12,000, about 14,000, about 16,000, about 18,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 52,000, about 54,000, about 56,000, about 58,000, about 60,000, about 62,000, about 64,000, about 66,000, about 68,000, about 70,000, about 72,000, about 74,000, about 76,000, about 78,000, about 80,000, about 82,000, about 84,000, about 86,000, about 88,000, about 90,000, about 92,000, about 94,000, about 96,000, about 98,000, about 100,000, or any range including and/or in between any two of the preceding values.

In any embodiment disclosed herein, the collagen of the second layer may comprise a weight ratio of human collagen type I to human collagen type III of about 100:0, about 90:10, about 80:20, about 70:30, about 60:40, about 50:50, about 40:60, about 30:70, about 20:80, about 10:90, about 0:100, or any range including and/or in between any two of the preceding values. Additionally or alternatively, in some embodiments, the ratio by weight of human collagen type I to human collagen type III is greater than about 50:50, or greater than about 70:30. Additionally or alternatively, in some embodiments, the collagen of the second layer may comprise a weight ratio of type I bovine collagen to type III bovine collagen of about 85:15.

Additionally or alternatively, in some embodiments, the oxidized cellulose of the second layer comprises oxidized regenerated cellulose (ORC). In any embodiment disclosed herein, ORC may be produced by the oxidation of cellulose, for example with dinitrogen tetroxide and/or as described in U.S. Pat. No. 3,122,479 (incorporated herein by reference). Without wishing to be bound by theory, it is believed that this process may convert primary alcohol groups on the saccharide residues of the celluolse to carboxylic acid groups, for example, forming uronic acid residues within the cellulose chain. The oxidation need not proceed with complete selectivity, and as a result hydroxyl groups on carbons 2 and 3 of the saccharide residue may be converted to the keto form. These ketone units may introduce an alkali labile link, which at pH 7 or higher initiates the decomposition of the polymer via formation of a lactone and sugar ring cleavage. As a result, oxidized regenerated cellulose is biodegradable and bioresorbable under physiological conditions. ORC is available with a variety of degrees of oxidation and hence rates of degradation.

In any embodiment disclosed herein, the ORC of the second layer may comprise about 30 wt. % to about 70 wt. %, with a weight-average molecular weight of about 10,000 to about 1,000,000. Additionally or alternatively, in some embodiments, the ORC in the second layer may comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, or any range including and/or in between any two of the preceding values. Additionally or alternatively, in some embodiments, the ORC of the second layer may comprise a weight-average molecular weight of about 10,000, about 11,000, about 12,000, about 13,000, about 14,000, about 15,000, about 16,000, about 17,000, about 18,000, about 19,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 55,000, about 60,000, about 65,000, about 70,000, about 75,000, about 80,000, about 85,000, about 90,000, about 95,000, about 100,000, about 110,000, about 120,000, about 130,000, about 140,000, about 150,000, about 160,000, about 170,000, about 180,000, about 190,000, about 200,000, about 210,000, about 220,000, about 230,000, about 240,000, about 250,000, about 260,000, about 270,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 460,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630, 000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, or any range including and/or in between any two of the preceding values.

The ORC may include particles, fibers, or both; in any embodiment disclosed herein, the ORC may be in the form of particles, such as fiber particles or powder particles. In embodiments that include ORC fibers, the ORC fibers may have a volume fraction such that at least 80% of the fibers have lengths in the range from about 5 µm to about 1,000 µm. Additionally or alternatively, in some embodiments, the ORC of the second layer may comprise fibers lengths of about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 22 µm, about 24 µm, about 26 µm, about 28 µm, about 30 µm, about 32 µm, about 34 µm, about 36 µm, about 38 µm, about 40 µm, about 42 µm, about 44 µm, about 46 µm, about 48 µm, about 50 µm, about 55 µm, about 60 µm, about 65 µm, about 70 µm, about 75 µm, about 80 µm, about 85 µm, about 90 µm, about 95 µm, about 100 µm, about 110 µm, about 120 µm, about 130 µm, about 140 µm, about 150 µm, about 160 µm, about 170 µm, about 180 µm, about 190 µm, about 200 µm, about 220 µm, about 230 µm, about 240 µm, about 250 µm, about 260 µm, about 280 µm, about 300 µm, about 320 µm, about 340 µm, about 360 µm, about 380 µm, about 400 µm, about 420 µm, about 440 µm, about 460 µm, about 480 µm, about 500 µm, about 550 µm, about 600 µm, about 650 µm, about 700 µm, about 750 µm, about 800 µm, about 850 µm, about 900 µm, about 950 µm, about 1,000 µm, or any range including and/or in between any two of the preceding values.

In any embodiment disclosed herein, the mixture of collagen and ORC within the second layer of the present technology may comprise about 30 wt. % to about 90 wt. %. Additionally or alternatively, in some embodiments, the collagen and ORC mixture of the second layer may comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, or any range including and/or in between any two of the preceding values.

In any embodiment disclosed herein, the mixture of collagen and ORC within the second layer of the present technology may comprise a ratio of about 90:10 to 10:90, or about 60:40 to about 40:60. Additionally or alternatively, in some embodiments, the mixture of collagen and ORC within the second layer may comprise a ratio of about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, or any range including and/or in between any two of the preceding values.

In any embodiment disclosed herein, the bacteria reducing active ingredient of the second layer may comprise an organic acid or a pharmaceutically acceptable salt thereof. Additionally or alternatively, in some embodiments, the bacteria reducing active ingredient of the second layer may be selected from the group consisting of citric acid, acetic acid, or any pharmaceutically acceptable salt thereof, and any combination thereof. Additionally or alternatively, in some embodiments, the bacteria reducing active ingredient of the second layer may be present in a concentration of about 50 mM to about 400 mM. Additionally or alternatively, in some embodiments, the bacteria reducing active ingredient of the second layer may be present in a concentration of about 50 mM, about 52 mM, about 54 mM, about 56 mM, about 58 mM, about 60 mM, about 62 mM, about 64 mM, about 66 mM, about 68 mM, about 70 mM, about 72 mM, about 74 mM, about 76 mM, about 78 mM, about 80 mM, about 82 mM, about 84 mM, about 86 mM, about 88 mM, about 90 mM, about 92 mM, about 94 mM, about 96 mM, about 98 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, or any range including and/or in between any two of the preceding values. Additionally or alternatively, in some embodiments, the bacteria reducing active ingredient of the second layer may be present in a concentration of about 100 mM to about 250 mM.

In any embodiment disclosed herein, the at least one bacteria reducing active ingredient of the second layer may be mixed with a solvent, wherein the solvent is water, a $(C_1-C_3)$alcohol or an aqueous solution thereof. Additionally or alternatively, in some embodiments, the $(C_1-C_3)$alcohol may be one or more of methanol, ethanol, propanol, isopropanol, or any combination thereof.

In any embodiment disclosed herein, the second layer may comprise about 0.1 wt. % to about 1 wt. %, or about 0.1 wt. % to about 3 wt. % of a silver compound. Additionally or alternatively, in some embodiments, the silver compound of the second layer may comprise about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.22 wt. %, about 0.24 wt. %, about 0.26 wt. %, about 0.28 wt. %, about 0.3 wt. %, about 0.32 wt. %, about 0.34 wt. %, about 0.36 wt. %, about 0.38 wt. %, about 0.4 wt. %, about 0.42 wt. %, about 0.44 wt. %, about 0.46 wt. %, about 0.48 wt. %, about 0.50 wt. %, about 0.52 wt. %, about 0.54 wt. %, about 0.56 wt. %, about 0.58 wt. %, about 0.6 wt. %, about 0.62 wt. %, about 0.64 wt. %, about 0.66 wt. %, about 0.68 wt. %, about 0.7 wt. %, about 0.72 wt. %, about 0.74 wt. %, about 0.76 wt. %, about 0.78 wt. %, about 0.8 wt. %, about 0.82 wt. %, about 0.84 wt. %, about 0.86 wt. %, about 0.88 wt. %, about 0.9 wt. %, about 0.92 wt. %, about 0.94 wt. %, about 0.96 wt. %, about 0.98 wt. %, about 1 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, about 1.5 wt. %, about 1.55 wt. %, about 1.6 wt. %, about 1.65 wt. %, about 1.7 wt. %, about 1.75 wt. %, about 1.8 wt. %, about 1.85 wt. %, about 1.9 wt. %, about 1.95 wt. %, about 2 wt. %, about 2.05 wt. %, about 2.1 wt. %, about 2.15 wt. %, about 2.2 wt. %, about 2.25 wt. %, about 2.3 wt. %, about 2.35 wt. %, about 2.4 wt. %, about 2.45 wt. %, about 2.5 wt. %, about 2.55 wt. %, about 2.6 wt. %, about 2.65 wt. %, about 2.7 wt. %, about 2.75 wt. %, about 2.8 wt. %, about 2.85 wt. %, about 2.9 wt. %, about 2.95 wt. %, about 3 wt. %, or any range including and/or in between any two of the preceding values. Additionally or alternatively, in some embodiments, the silver compound of the second layer comprises one or more pharmaceutically acceptable silver salts. Exemplary sources of the one or more pharmaceutically acceptable silver salts of the second layer include, but are not limited to, silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, silver p-aminosalicylate, nanocrystalline silver, or any combination thereof. Additionally or alternatively, in some embodiments, at least a portion of any silver compound of the second layer may be present as a complex of anionic polysaccharide with the silver compound (e.g., an ORC-silver complex).

In any embodiment disclosed herein, the second layer may comprise about 1 wt. % to about 25 wt. % of one or more additional biomaterials. Additionally or alternatively, in some embodiments, the one or more additional biomaterials of the second layer may comprise about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, or any range including and/or in between any two of the preceding values. Additionally or alternatively, in some embodiments, the one or more additional biomaterials included in the second layer may be selected from the group consisting of gelatin, chitosan, fibronectin, hyaluronic acid, polysaccharides, and any combination thereof.

In any embodiment disclosed herein, the second layer may comprise about 1 wt. % to about 10 wt. %, or about 1 wt. % to about 15 wt. % of at least one plasticizer. Additionally or alternatively, in some embodiments, the at least one plasticizer of the second layer may comprise about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.2 wt. %, about 2.4 wt. %, about 2.6 wt. %, about 2.8 wt. %, about 3 wt. %, about 3.2 wt. %, about 3.4 wt. %, about 3.6 wt. %, about 3.8 wt. %, about 4 wt. %, about 4.2 wt. %, about 4.4 wt. %, about 4.6 wt. %, about 4.8 wt. %, about 5 wt. %, about 5.2 wt. %, about 5.4 wt. %, about 5.6 wt. %, about 5.8 wt. %, about 6 wt. %, about 6.2 wt. %, about 6.4 wt. %, about 6.6 wt. %, about 6.8 wt. %, about 7 wt. %, about 7.2 wt. %, about 7.4 wt. %, about 7.6 wt. %, about 7.8 wt. %, about 8 wt. %, about 8.2 wt. %, about 8.4 wt. %, about 8.6 wt. %, about 8.8 wt. %, about 9 wt. %, about 9.2 wt. %, about 9.4 wt. %, about 9.6 wt. %, about 9.8 wt. %, about 10 wt. %, about 10.2 wt. %, about 10.4 wt. %, about 10.6 wt. %, about 10.8 wt. %, about 11 wt. %, about 11.2 wt. %, about 11.4 wt. %, about 11.6 wt. %, about 11.8 wt. %, about 12 wt. %, about 12.2 wt. %, about 12.4 wt. %, about 12.6 wt. %, about 12.8 wt. %, about 13 wt. %, about 13.2 wt. %, about 13.4 wt. %, about 13.6 wt. %, about 13.8 wt. %, about 14 wt. %, about 14.2 wt. %, about 14.4 wt. %, about 14.6 wt. %, about 14.8 wt. %, about 15 wt. %, or any range including and/or in between any two of the preceding values. Exemplary plasticizers include, but are not limited to, an acetylated monoglyceride, an alkyl citrate, methyl ricinoleate, glycerol, polyvinylpyrrolidone, or any combination thereof. Examples of alkyl citrates include, but are not limited to, triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, or any combination thereof.

In any embodiment disclosed herein, the solid content of the second layer may comprise about 2 wt. % to about 10 wt. %, or about 4 wt. % to about 10 wt. %. Additionally or alternatively, in some embodiments, the solid content of the second layer may comprise about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.4 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, or any range including and/or in between any two of the preceding values.

The Optional Layers

As used herein, the term "optional layer(s)" refers to a wound dressing composition of any embodiment disclosed herein, further comprising a third layer with or without a fourth layer.

The present disclosure provides a wound dressing composition comprising an optional layer(s) wherein the optional layer(s) comprises a homogeneous mixture of a collagen, an oxidized cellulose, and a silver compound.

In any embodiment disclosed herein, the optional layer(s) comprises a wound-facing side and an environmental-facing side.

In any embodiment disclosed herein, the collagen of the optional layer(s) may comprise mammalian collagen. Additionally or alternatively, in some embodiments, the collagen of the optional layer(s) may comprise a human collagen. Additionally or alternatively, in some embodiments, the human collagen may comprise human collagen type I and human collagen type III. Additionally or alternatively, in some embodiments, the collagen of the optional layer(s) may comprise a bovine collagen. Additionally or alternatively, in some embodiments, the collagen of the optional layer(s) may comprise bovine collagen type I, bovine collagen type II, bovine collagen type III, and bovine collagen type IV. Additionally or alternatively, in some embodiments, the collagen of the optional layer(s) may comprise bovine collagen type I and bovine collagen type III.

In any embodiment disclosed herein, the collagen of the optional layer(s) may be provided by any manner known in the art. Additionally or alternatively, in some embodiments, the collagen may be provided by a tissue sample or recombinantly manufactured. Additionally or alternatively, in some embodiments, mammalian recombinant collagen of the optional layer(s) may be provided by any suitable method known in the art. Additionally or alternatively, in some embodiments, human recombinant collagen of the optional layer(s) may be provided by any suitable method known in the art. For example, the step of providing human recombinant collagen may comprise following the protocol described in U.S. Pat. No. 5,962,648, the entire content of which is incorporated herein by reference. Further recombinant processes are set forth in U.S. Pat. No. 5,593,859 and WO2004/078120, which are also incorporated herein by reference. Additionally or alternatively, in some embodiments, collagen will be recombinantly manufactured by culturing a cell which has been transfected with at least one gene encoding a polypeptide comprising collagen and genes encoding oxidized cellulose and subunits of the post-translational enzyme prolyl 4-hydroxylase, and purifying the resultant collagen monomer therefrom. Additionally or alternatively, in some embodiments, collagen will be recombinantly manufactured by a plant (e.g., CollPlant, CollPlant Holdings Ltd., Ness Ziona, Israel) such as tobacco, or in yeast. The human recombinant collagen solution may be subsequently subjected to polymerization or cross-linking conditions to produce an insoluble fibrous collagen.

In any embodiment disclosed herein, the collagen may be a type I collagen, a type II collagen, or a type III collagen. Additionally or alternatively, in some embodiments, the collagen may be obtained from any natural source, may be chemically-modified collagen (e.g., an atelocollagen obtained by removing the immunogenic telopeptides from natural collagen), or may be any combination thereof. For example, the collagen may include collagen obtained from bovine corium that has been rendered largely free of non-collagenous components, for example, including fat, non-collagenous proteins, polysaccharides, and other carbohydrates, such as by procedures described in U.S. Pat. Nos. 4,614,794 and 4,320,201, the entire contents of which are incorporated by reference.

In any embodiment disclosed herein, the collagen of the optional layer(s) may comprise about 0.1 wt. % to about 60 wt. %, or about 30 wt. % to about 95 wt. %, with a weight-average molecular weight of about 5,000 to about 100,000. Additionally or alternatively, in some embodiments, the amount of collagen in the optional layer(s) may be about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.2 wt. %, about 2.4 wt. %, about 2.6 wt. %, about 2.8 wt. %, about 3 wt. %, about 3.2 wt. %, about 3.4 wt. %, about 3.6 wt. %, about 3.8 wt. %, about 4 wt. %, about 4.2 wt. %, about 4.4 wt. %, about 4.6 wt. %, about 4.8 wt. %, about 5 wt. %, about 5.2 wt. %, about 5.4 wt. %, about 5.6 wt. %, about 5.8 wt. %, about 6 wt. %, about 6.2 wt. %, about 6.4 wt. %, about 6.6 wt. %, about 6.8 wt. %, about 7 wt. %, about 7.2 wt. %, about 7.4 wt. %, about 7.6 wt. %, about 7.8 wt. %, about 8 wt. %, about 8.2 wt. %, about 8.4 wt. %, about 8.6 wt. %, about 8.8 wt. %, about 9 wt. %, about 9.2 wt. %, about 9.4 wt. %, about 9.6 wt. %, about 9.8 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, about 92 wt. %, about 94 wt. %, about 95 wt. %, or any range including and/or in between any two of the preceding values. Additionally or alternatively, in some embodiments, the collagen of the optional layer(s) comprises a weight-average molecular weight of about 5,000, about 6,000, about 7,000, about 8,000, about 9,000, about 10,000, about 12,000, about 14,000, about 16,000, about 18,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 52,000, about 54,000, about 56,000, about 58,000, about 60,000, about 62,000, about 64,000, about 66,000, about 68,000, about 70,000, about 72,000, about 74,000, about 76,000, about 78,000, about 80,000, about 82,000, about 84,000, about 86,000, about 88,000, about 90,000, about 92,000, about 94,000, about 96,000, about 98,000, about 100,000, or any range including and/or in between any two of the preceding values.

In any embodiment disclosed herein, the collagen of the optional layer(s) may comprise a weight ratio of human collagen type I to human collagen type III of about 100:0, about 90:10, about 80:20, about 70:30, about 60:40, about 50:50, about 40:60, about 30:70, about 20:80, about 10:90, about 0:100, or any range including and/or in between any two of the preceding values. Additionally or alternatively, in some embodiments, the ratio by weight of human collagen type I to human collagen type III is greater than about 50:50, or greater than about 70:30. Additionally or alternatively, in some embodiments, the collagen of the optional layer(s) may comprise a weight ratio of type I bovine collagen to type III bovine collagen of about 85:15.

Additionally or alternatively, in some embodiments, the oxidized cellulose of the optional layer(s) comprises oxidized regenerated cellulose (ORC). In any embodiment disclosed herein, ORC may be produced by the oxidation of cellulose, for example with dinitrogen tetroxide and/or as described in U.S. Pat. No. 3,122,479 (incorporated herein by reference). Without wishing to be bound by theory, it is believed that this process may convert primary alcohol groups on the saccharide residues of the celluolse to carboxylic acid groups, for example, forming uronic acid residues within the cellulose chain. The oxidation need not proceed with complete selectivity, and as a result hydroxyl groups on carbons 2 and 3 of the saccharide residue may be converted to the keto form. These ketone units may introduce an alkali labile link, which at pH 7 or higher initiates the decomposition of the polymer via formation of a lactone and sugar ring cleavage. As a result, oxidized regenerated cellulose is biodegradable and bioresorbable under physiological conditions. ORC is available with a variety of degrees of oxidation and hence rates of degradation.

In any embodiment disclosed herein, the ORC of the optional layer(s) may comprise about 30 wt. % to about 70 wt. %, with a weight-average molecular weight of about 10,000 to about 1,000,000. Additionally or alternatively, in some embodiments, the ORC in the optional layer(s) may comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, or any range including and/or in between any two of the preceding values. Additionally or alternatively, in some embodiments, the ORC of the optional layer(s) may comprise a weight-average molecular weight of about 10,000, about 11,000, about 12,000, about 13,000, about 14,000, about 15,000, about 16,000, about 17,000, about 18,000, about 19,000, about 20,000, about 22,000, about 24,000, about 26,000, about 28,000, about 30,000, about 32,000, about 34,000, about 36,000, about 38,000, about 40,000, about 42,000, about 44,000, about 46,000, about 48,000, about 50,000, about 55,000, about 60,000, about 65,000, about 70,000, about 75,000, about 80,000, about 85,000, about 90,000, about 95,000, about 100,000, about 110,000, about 120,000, about 130,000, about 140,000, about 150,000, about 160,000, about 170,000, about 180,000, about 190,000, about 200,000, about 210,000, about 220,000, about 230,000, about 240,000, about 250,000, about 260,000, about 270,000, about 280,000, about 290,000, about 300,000, about 310,000, about 320,000, about 330,000, about 340,000, about 350,000, about 360,000, about 370,000, about 380,000, about 390,000, about 400,000, about 410,000, about 420,000, about 430,000, about 440,000, about 450,000, about 460,000, about 470,000, about 480,000, about 490,000, about 500,000, about 510,000, about 520,000, about 530,000, about 540,000, about 550,000, about 560,000, about 570,000, about 580,000, about 590,000, about 600,000, about 610,000, about 620,000, about 630,000, about 640,000, about 650,000, about 660,000, about 670,000, about 680,000, about 690,000, about 700,000, about 710,000, about 720,000, about 730,000, about 740,000, about 750,000, about 760,000, about 770,000, about 780,000, about 790,000, about 800,000, about 810,000, about 820,000, about 830,000, about 840,000, about 850,000, about 860,000, about 870,000, about 880,000, about 890,000, about 900,000, about 910,000, about 920,000, about 930,000, about 940,000, about 950,000, about 960,000, about 970,000, about 980,000, about 990,000, about 1,000,000, or any range including and/or in between any two of the preceding values.

The ORC may include particles, fibers, or both; in any embodiment disclosed herein, the ORC may be in the form of particles, such as fiber particles or powder particles. In embodiments that include ORC fibers, the ORC fibers may have a volume fraction such that at least 80% of the fibers have lengths in the range from about 5 μm to about 1,000 μm. Additionally or alternatively, in some embodiments, the ORC of the optional layer(s) may comprise fibers lengths of about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 22 μm, about 24 μm, about 26 μm, about 28 μm, about 30 μm, about 32 μm, about 34 μm, about 36 μm, about 38 μm, about 40 μm, about 42 μm, about 44 μm, about 46 μm, about 48 μm, about 50 μm, about 55 μm, about 60 μm, about 65 μm, about 70 μm, about 75 μm, about 80 μm, about 85 μm, about 90 μm, about 95 μm, about 100 μm, about 110 μm, about 120 μm, about 130 μm, about 140 μm, about 150 μm, about 160 μm, about 170 μm, about 180 μm, about 190 μm, about 200 μm, about 220 μm, about 230 μm, about 240 μm, about 250 μm, about 260 μm, about 280 μm, about 300 μm, about 320 μm, about 340 μm, about 360 μm, about 380 μm, about 400 μm, about 420 μm, about 440 μm, about 460 μm, about 480 μm, about 500 μm, about 550 μm, about 600 μm, about 650 μm, about 700 μm, about 750 μm, about 800 μm, about 850 μm, about 900 μm, about 950 μm, about 1,000 μm, or any range including and/or in between any two of the preceding values.

In any embodiment disclosed herein, the mixture of collagen and ORC within the optional layer(s) of the present technology may comprise about 30 wt. % to about 90 wt. %. Additionally or alternatively, in some embodiments, the collagen and ORC mixture of the optional layer(s) may comprise about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, or any range including and/or in between any two of the preceding values.

In any embodiment disclosed herein, the mixture of collagen and ORC within the optional layer(s) of the present technology may comprise a ratio of about 90:10 to 10:90, or about 60:40 to about 40:60. Additionally or alternatively, in some embodiments, the mixture of collagen and ORC within the optional layer(s) may comprise a ratio of about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, or any range including and/or in between any two of the preceding values.

In any embodiment disclosed herein, the optional layer(s) may comprise about 0.1 wt. % to about 3 wt. % of a silver compound. Additionally or alternatively, in some embodiments, the silver compound of the optional layer(s) may comprise about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.22 wt. %, about 0.24 wt. %, about 0.26 wt. %, about 0.28 wt. %, about 0.3 wt. %, about 0.32 wt. %, about 0.34 wt. %, about 0.36 wt. %, about 0.38 wt. %, about 0.4 wt. %, about 0.42 wt. %, about 0.44 wt. %, about 0.46 wt. %, about 0.48 wt. %, about 0.50 wt. %, about 0.52 wt. %, about 0.54 wt. %, about 0.56 wt. %, about 0.58 wt. %, about 0.6 wt. %, about 0.62 wt. %, about 0.64 wt. %, about 0.66 wt. %, about 0.68 wt. %, about 0.7 wt. %, about 0.72 wt. %, about 0.74 wt. %, about 0.76 wt. %, about 0.78 wt. %, about 0.8 wt. %, about 0.82 wt. %, about 0.84 wt. %, about 0.86 wt. %, about 0.88 wt. %, about 0.9 wt. %, about 0.92 wt. %, about 0.94 wt. %, about 0.96 wt. %, about 0.98 wt. %, about 1 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, about 1.5 wt. %, about 1.55 wt. %, about 1.6 wt. %, about 1.65 wt. %, about 1.7 wt. %, about 1.75 wt. %, about 1.8 wt. %, about 1.85 wt. %, about 1.9 wt. %, about 1.95 wt. %, about 2 wt. %, about 2.05 wt. %, about 2.1 wt. %, about 2.15 wt. %, about 2.2 wt. %, about 2.25 wt. %, about 2.3 wt. %, about 2.35 wt. %, about 2.4 wt. %, about 2.45 wt. %, about 2.5 wt. %, about 2.55 wt. %, about 2.6 wt. %, about 2.65 wt. %, about 2.7 wt. %, about 2.75 wt. %, about 2.8 wt. %, about 2.85 wt. %, about 2.9 wt. %, about 2.95 wt. %, about 3 wt. %, or any range including and/or in between any two of the preceding values. Additionally or alternatively, in some embodiments, the silver compound of the optional layer(s) comprises one or more pharmaceutically acceptable silver salts. Exemplary sources of the one or more pharmaceutically acceptable silver salts of the optional layer(s) include, but are not limited to, silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, silver p-aminosalicylate, nanocrystalline silver, or any combination thereof. Additionally or alternatively, in some embodiments, at least a portion of any silver compound of the optional layer(s) may be present as a complex of anionic polysaccharide with the silver compound (e.g., an ORC-silver complex).

In any embodiment disclosed herein, the optional layer(s) may comprise about 1 wt. % to about 25 wt. % of one or more additional biomaterials. Additionally or alternatively, in some embodiments, the one or more additional biomaterials of the optional layer(s) may comprise about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, or any range including and/or in between any two of the preceding values. Additionally or alternatively, in some embodiments, the one or more additional biomaterials included in the optional layer(s) may be selected from the group consisting of gelatin, chitosan, fibronectin, hyaluronic acid, polysaccharides, and any combination thereof.

In any embodiment disclosed herein, the optional layer(s) may comprise about 1 wt. % to about 10 wt. %, or about 1 wt. % to about 15 wt. % of at least one plasticizer. Additionally or alternatively, in some embodiments, the at least one plasticizer of the optional layer(s) may comprise about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.2 wt. %, about 2.4 wt. %, about 2.6 wt. %, about 2.8 wt. %, about 3 wt. %, about 3.2 wt. %, about 3.4 wt. %, about 3.6 wt. %, about 3.8 wt. %, about 4 wt. %, about 4.2 wt. %, about 4.4 wt. %, about 4.6 wt. %, about 4.8 wt. %, about 5 wt. %, about 5.2 wt. %, about 5.4 wt. %, about 5.6 wt. %, about 5.8 wt. %, about 6 wt. %, about 6.2 wt. %, about 6.4 wt. %, about 6.6 wt. %, about 6.8 wt. %, about 7 wt. %, about 7.2 wt. %, about 7.4 wt. %, about 7.6 wt. %, about 7.8 wt. %, about 8 wt. %, about 8.2 wt. %, about 8.4 wt. %, about 8.6 wt. %, about 8.8 wt. %, about 9 wt. %, about 9.2 wt. %, about 9.4 wt. %, about 9.6 wt. %, about 9.8 wt. %, about 10 wt. %, about 10.2 wt. %, about 10.4 wt. %, about 10.6 wt. %, about 10.8 wt. %, about 11 wt. %, about 11.2 wt. %, about 11.4 wt. %, about 11.6 wt. %, about 11.8 wt. %, about 12 wt. %, about 12.2 wt. %, about 12.4 wt. %, about 12.6 wt. %, about 12.8 wt. %, about 13 wt. %, about 13.2 wt. %, about 13.4 wt. %, about 13.6 wt. %, about 13.8 wt. %, about 14 wt. %, about 14.2 wt. %, about 14.4 wt. %, about 14.6 wt. %, about 14.8 wt. %, about 15 wt. %, or any range including and/or in between any two of the preceding values. Exemplary plasticizers include, but are not limited to, an acetylated monoglyceride, an alkyl citrate, methyl ricinoleate, glycerol, polyvinylpyrrolidone, or any combination thereof. Examples of alkyl citrates include, but are not limited to, triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, or any combination thereof.

In any embodiment disclosed herein, the solid content of the optional layer(s) may comprise about 0.1 wt. % to about 10 wt. %. Additionally or alternatively, in some embodiments, the solid content of the optional layer(s) may comprise about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.22 wt. %, about 0.24 wt. %, about 0.26 wt. %, about 0.28 wt. %, about 0.3 wt. %, about 0.32 wt. %, about 0.34 wt. %, about 0.36 wt. %, about 0.38 wt. %, about 0.4 wt. %, about 0.42 wt. %, about 0.44 wt. %, about 0.46 wt. %, about 0.48 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.4 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, or any range including and/or in between any two of the preceding values.

The Wound Dressing Composition

The present disclosure provides a wound dressing composition comprising the first layer and the second layer disclosed herein. Additionally or alternatively, in some embodiments, the present disclosure provides a wound dressing composition comprising the first layer disclosed herein, the second layer disclosed herein, and the optional layer(s) disclosed herein. Each of the first layer, the second, and the optional layers independently comprise a wound-facing side and an environmental-facing side.

In some embodiments, the wound-facing side of the second layer is coupled with the environmental-facing side of the first layer.

Additionally or alternatively, in some embodiments, the wound-facing side of the optional third layer is coupled with the environmental-facing side of the second layer, and wherein the wound-facing side of the second layer is coupled with the environmental-facing side of the first layer.

Additionally or alternatively, in some embodiments, the wound-facing side of the optional fourth layer is coupled with the environmental-facing side of the optional third layer, the wound-facing side of the optional third layer is coupled with the environmental-facing side of the second layer, and wherein the wound-facing side of the second layer is coupled with the environmental-facing side of the first layer.

In any embodiment disclosed herein, the wound dressing composition comprises the first layer and the second layer wherein the first layer and the second layer are adjoined. Additionally or alternatively, in some embodiments, the first layer may be in the form of a freeze-dried sponge or a film material. Additionally or alternatively, in some embodiments, the second layer may be in the form of a freeze-dried sponge or a film material. In any embodiment disclosed herein, a suitable sponge is made by freeze-drying or solvent drying an aqueous dispersion consisting essentially of mammalian recombinant collagen particles or fibers and ORC fibers, together with suitable therapeutic agents. Additionally or alternatively, in some embodiments, the wound dressing compositions of the present technology are freeze-dried sponges of human recombinant collagen and ORC substantially as described in EP-A-1153622, the entire content of which is incorporated herein by reference.

In any embodiment disclosed herein, the wound dressing composition comprises the first layer and the second layer, wherein the first layer and the second layer are not adjoined. Additionally or alternatively, in some embodiments, the wound dressing composition may be in the form of a freeze-dried sponge or a film material. In any embodiment disclosed herein, a suitable sponge is made by freeze-drying or solvent drying an aqueous dispersion consisting essentially of mammalian recombinant collagen particles or fibers and ORC fibers, together with suitable therapeutic agents. Additionally or alternatively, in some embodiments, the wound dressing composition of the present technology are freeze-dried sponges of human recombinant collagen and ORC substantially as described in EP-A-1153622 (supra).

In any embodiment disclosed herein, the average pore size of the freeze-dried sponge is about 10-500 µm, or about 100-300 µm. Additionally or alternatively, in some embodiments, the average pore size of the freeze-dried sponge is about 10 µm, about 12 µm, about 14 µm, about 16 µm, about 18 µm, about 20 µm, about 22 µm, about 24 µm, about 26 µm, about 28 µm, about 30 µm, about 32 µm, about 34 µm, about 36 µm, about 38 µm, about 40 µm, about 42 µm, about 44 µm, about 46 µm, about 48 µm, about 50 µm, about 52 µm, about 54 µm, about 56 µm, about 58 µm, about 60 µm, about 62 µm, about 64 µm, about 66 µm, about 68 µm, about 70 µm, about 72 µm, about 74 µm, about 76 µm, about 78 µm, about 80 µm, about 82 µm, about 84 µm, about 86 µm, about 88 µm, about 90 µm, about 92 µm, about 94 µm, about 96 µm, about 98 µm, about 100 µm, about 105 µm, about 110 µm, about 115 µm, about 120 µm, about 125 µm, about 130 µm, about 135 µm, about 140 µm, about 145 µm, about 150 µm, about 155 µm, about 160 µm, about 165 µm, about 170 µm, about 175 µm, about 180 µm, about 185 µm, about 190 µm, about 195 µm, about 200 µm, about 210 µm, about 220 µm, about 230 µm, about 240 µm, about 250 µm, about 260 µm, about 270 µm, about 280 µm, about 290 µm, about 300 µm, or any range including and/or in between any two of the preceding values.

In some embodiments, the wound dressing composition of the present disclosure is sterile and packaged in a microorganism-impermeable container.

In any embodiment disclosed herein, the wound dressing composition of the present technology is capable of preventing, reducing, inhibiting, or disrupting biofilm formation in a wound. Reducing a biofilm includes reducing the number of total viable microorganisms making up at least part of the biofilm, for example, as measured by total viable counts (TVC) of microorganisms (e.g., bacteria, yeast). The biofilm may comprise bacteria including, but not limited to *Pseudomonas aeruginosa*, *Staphylococcus aureus* and *Streptococcus mutans*. The biofilm may also include fungi including but not limited to yeasts, such as *Candida albicans*. Additionally or alternatively, in some embodiments, the wound dressing composition of the present technology may be capable of preventing, reducing, inhibiting, or disrupting a biofilm in a wound by ≥about 10% to ≥about 100% after about 12 hours to about 24 hours in vitro exposure, or by ≥about 1 $\log_{10}$ units to by ≥about 6 $\log_{10}$ units after about 12 hours to about 24 hours in vitro exposure, compared to that observed in a wound of a control patient that does not receive the wound dressing composition of the present technology. Additionally or alternatively, in some embodiments, the wound dressing composition of the present technology may be capable of preventing, reducing, inhibiting, or disrupting a biofilm in a wound by ≥about 10%, ≥about 15%, ≥about 20%, ≥about 25%, ≥about 30%, ≥about 35%, ≥about 40%, ≥about 45%, ≥about 50%, ≥about 55%, ≥about 60%, ≥about 65%, ≥about 70%, ≥about 75%, ≥about 80%, ≥about 85%, ≥about 90%, ≥about 95%, ≥about 99%, ≥about 100%, or any range including and/or in between any two of the preceding values, compared to that observed in a wound of a control patient that does not receive the wound dressing composition of the present technology. Additionally or alternatively, in some embodiments, the wound dressing composition of the present technology may be capable of preventing, reducing, inhibiting, or disrupting a biofilm in a wound by ≥about 1 $\log_{10}$ units, by ≥about 1.5 $\log_{10}$ units, by ≥about 2 $\log_{10}$ units, by ≥about 2.5 $\log_{10}$ units, by ≥about 3 $\log_{10}$ units, by ≥about 3.5 $\log_{10}$ units, by ≥about 4 $\log_{10}$ units, by ≥about 4.5 $\log_{10}$ units, by ≥about 5 $\log_{10}$ units, by ≥about 5.5 $\log_{10}$ units, by ≥about 6 $\log_{10}$ units, or any range including and/or in between any two of the preceding values, compared to that observed in a wound of a control patient that does not receive the wound dressing composition of the present technology.

In any embodiment disclosed herein, the wound dressing composition exhibits about 10% to about 100% reduction in tackiness observed compared to that observed with a control wound dressing prepared with water. Additionally or alternatively, in some embodiments, the wound dressing composition exhibits about 10%, about 11%, about 12%, about 13%, about 14%, about 15%, about 16%, about 17%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, about 100%, or any range including and/or in between any two of the preceding values, reduction in tackiness observed compared to that observed with a control wound dressing prepared with water.

The therapeutic efficacy of the wound dressing composition of the present technology can be assayed using any method known to those in the art. An exemplary method to test the therapeutic efficacy of the wound dressing composition of the present technology is the colony drip flow reactor (C-DFR) assay (see Lipp, C., et al., *J. Wound Care*, 19:220-226(2010)).

To prepare the reactor apparatus, absorbent pads can be glued with silicon-based aquarium sealant to clean glass microscope slides and placed in the channels of the C-DFR (Biosurface Technology, Bozeman, MT). The entire set-up was autoclaved and maintained sterile until use. A non-antimicrobial dressing (gauze) was included as a control in each experiment.

Experiments began by hydrating the absorbent pads with 0.5 ml of SWF and then 0.22 µm porous polycarbonate membranes (Sigma, Dorset, UK) were placed on these absorbent pads. Next, the membranes were inoculated with 10 µl of a Tryptone Soya broth (TSB)-diluted overnight culture (0.5 McFarland standard suspension). The system was left undisturbed for 30 minutes while the inoculum was allowed to dry. The reactor was then attached to a medium reservoir and Simulated Wound Fluid (SWF) was pumped through the system at 5 ml/h/channel. This reactor and set-up allowed the medium to drip down the microscope slide and absorb into the pad, which then supplied nutrients to the bacteria growing on the top side of membrane. The bacteria were then allowed to grow for 72 hours.

After the growth period, one biofilm/membrane per model was subjected to plate counting (see below) to enumerate the biofilm population pre-antimicrobial exposure. For each of the other channels, a sterile sample of biomaterial was placed directly on top of the biofilm/membrane. Dressings were moistened with simulated wound fluid (SWF) to simulate clinical usage. The assay continued for a further 24 hours (flow rate 5 ml/hr/channel), before the dressings were removed and the biofilm/membranes examined with plate counts to enumerate remaining biofilm after antimicrobial exposure. Samples of biofilm/membrane pre-antimicrobial exposure were also subjected to scanning electron microscopy (SEM).

After removal from the C-DFR, biofilm/membranes were rinsed three times with sterile phosphate buffered saline (PBS) to remove any adherent vegetative cells. Samples were added to Dey-Engley neutralising broth to negate any residual antimicrobial effect resulting from dressing contact. The samples were then subjected to 3 minutes of high speed vortexing. Serial 10-fold dilutions were made using sterile Dulbecco's Phosphate Buffered Saline (DPBS), and the dilutions were plated on Trypton Soya Agar (TSA) plates. After 24 hours of incubation at 37° C., the plates were counted and the number of colony forming units (CFU) per membrane was calculated.

Therapeutic and Prophylactic Methods of the Present Technology

In one aspect, the present disclosure provides a method for treating a wound in a subject in need thereof, wherein the method comprises administering to the wound a wound dressing composition of any embodiment disclosed herein. Additionally or alternatively, in some embodiments, the wound may be an acute wound or a chronic wound. Additionally or alternatively, in some embodiments, the wound is an acute wound selected from the group consisting of burns, skin grafts, and dehisced surgical wounds. Additionally or alternatively, in some embodiments, the wound is a chronic wound selected from the group consisting of infectious wounds, venous ulcers, arterial ulcers, decubitis ulcers and diabetic ulcers. In some embodiments, the wound dressing protects the wound from infection. The infection may be a bacterial infection or a fungal infection. In some embodiments, the bacterial infection is caused by gram-negative or gram-positive bacteria.

Examples of gram-positive bacteria include, but are not limited to *Actinomyces* sp., *Arcanobacterium* sp., *Bacillus* sp., *Bavariicoccus* sp., *Brachybacterium* sp., *Clostridium* sp., *Cnuibacter* sp., *Corynebacterium* sp., *Enterococcus* sp., *Desulfitobacterium* sp., *Fervidobacterium* sp., *Georgenia* sp., *Janibacter* sp., *Lactobacillales* sp., *Microbispora* sp., *Nocardia* sp., *Pasteuria* sp., *Pilibacter* sp., *Propionibacterium* sp., *Rathayibacter* sp., *Rhodococcus* sp., *Roseburia* sp., *Rothia* sp., *Sarcina* sp., *Solibacillus* sp., *Sporosarcina* sp., *Staphylococcus* sp., *Streptococcus* sp., *Syntrophomonas* sp., or *Tepidibacter* sp.

Examples of gram-negative bacteria include, but are not limited to *Acetobacter* sp., *Acidaminococcus* sp., *Acinetobacter* sp., *Agrobacterium* sp., *Akkermansia* sp., *Anaerobiospirillum* sp., *Anaerolinea* sp., *Arcobacter* sp., *Armatimonas* sp., *Azotobacter* sp., *Bacteroides* sp., *Bacteroidetes* sp., *Bartonella* sp., *Bdellovibriosp.*, *Brachyspira* sp., *Bradyrhizobium* sp., *Caldilinea* sp., *Cardiobacterium* sp., *Christensenella* sp., *Chthonomonas* sp., *Coxiella* sp., *Cyanobacteria* sp., *Cytophaga* sp., *Dehalogenimonas* sp., *Desulfurobacterium* sp., *Devosia* sp., *Dialister* sp., *Diciyoglomus* sp., *Dinoroseobacter* sp., *Enterobacter* sp., *Escherichia* sp., *Fimbriimonas* sp., *Flavobacterium* sp., *Francisella* sp., *Fusobacterium* sp., *Gluconacetobacter* sp., *Haemophilus* sp., *Helicobacter* sp., *Kingella* sp., *Klebsiella* sp., *Kluyvera* sp., *Kozakia* sp., *Legionella* sp. *Leptonema* sp. *Leptotrichia* sp., *Levilinea* sp. *Luteimonas* sp. *Megamonas* sp., *Megasphaera* sp., *Meiothermus* sp., *Methylobacterium* sp., *Moraxella* sp., *Morganella* sp., *Mycoplasma* sp., *Neisseria* sp., *Nitrosomonas* sp., *Pectinatus* sp., *Pedobacter* sp., *Pelosinus* sp., *Propionispora* sp., *Proteus* sp., *Pseudomonas* sp., *Pseudoxanthomonas* sp., *Rickettsia* sp., *Salinibacter* sp., *Salmonella* sp., *Samsonia* sp., *Serratia* sp., *Shigella* sp., *Shimwellia* sp., *Sphingomonas* sp., *Stenotrophomonas* sp., *Thorselliaceae* sp., *Vampirococcus* sp., *Verminephrobacter* sp., *Vibrio* sp., *Victivallis* sp., *Vitreoscilla* sp., *Wolbachia* sp.

Additionally or alternatively, in some embodiments, the fungal infection is caused by a fungus selected from the group consisting of *Aspergillus* sp., *Aureobasidium* sp., *Candida* sp., *Cladosporium* sp., *Curvularia* sp., *Engodontium* sp., *Epicoccum* sp., *Gibberella* sp., *Hypocreales* sp., *Leptosphaerulina* sp., *Malessezia* sp., *Penicillium* sp., *Rhodosporidium* sp., *Trichosporon* sp., *Trichtophyton* sp., and *Ulocladium* sp.

Additionally or alternatively, in some embodiments, the wound comprises a biofilm and the wound dressing composition of the present technology prevents, reduces, inhibits, or disrupts the biofilm.

In one aspect, the present disclosure provides a method for maintaining reduced biofilm levels in a wound in a subject in need thereof, wherein the method comprises administering to the wound a wound dressing composition of any embodiment disclosed herein. Additionally or alternatively, in some embodiments, the wound may be an acute wound or a chronic wound. Additionally or alternatively, in some embodiments, the wound is an acute wound selected from the group consisting of burns, skin grafts, and dehisced surgical wounds. Additionally or alternatively, in some embodiments, the wound is a chronic wound selected from the group consisting of infectious wounds, venous ulcers, arterial ulcers, decubitis ulcers and diabetic ulcers. In some embodiments, the wound dressing protects the wound from infection. The infection may be a bacterial infection or a fungal infection. In some embodiments, the bacterial infection is caused by gram-negative or gram-positive bacteria.

Examples of gram-positive bacteria include, but are not limited to *Actinomyces* sp., *Arcanobacterium* sp., *Bacillus* sp., *Bavariicoccus* sp., *Brachybacterium* sp., *Clostridium* sp., *Cnuibacter* sp., *Corynebacterium* sp., *Enterococcus* sp., *Desulfitobacterium* sp., *Fervidobacterium* sp., *Georgenia* sp., *Janibacter* sp., *Lactobacillales* sp., *Microbispora* sp.,

*Nocardia* sp., *Pasteuria* sp., *Pilibacter* sp., *Propionibacterium* sp., *Rathayibacter* sp., *Rhodococcus* sp., *Roseburia* sp., *Rothia* sp., *Sarcina* sp., *Solibacillus* sp., *Sporosarcina* sp., *Staphylococcus* sp., *Streptococcus* sp., *Syntrophomonas* sp., or *Tepidibacter* sp.

Examples of gram-negative bacteria include, but are not limited to *Acetobacter* sp., *Acidaminococcus* sp., *Acinetobacter* sp., *Agrobacterium* sp., *Akkermansia* sp., *Anaerobiospirillum* sp., *Anaerolinea* sp., *Arcobacter* sp., *Armatimonas* sp., *Azotobacter* sp., *Bacteroides* sp., *Bacteroidetes* sp., *Bartonella* sp., *Bdellovibriosp.*, *Brachyspira* sp., *Bradyrhizobium* sp., *Caldilinea* sp., *Cardiobacterium* sp., *Christensenella* sp., *Chthonomonas* sp., *Coxiella* sp., *Cyanobacteria* sp., *Cytophaga* sp., *Dehalogenimonas* sp., *Desulfurobacterium* sp., *Devosia* sp., *Dialister* sp., *Diciyoglomus* sp., *Dinoroseobacter* sp., *Enterobacter* sp., *Escherichia* sp., *Fimbriimonas* sp., *Flavobacterium* sp., *Francisella* sp., *Fusobacterium* sp., *Gluconacetobacter* sp., *Haemophilus* sp., *Helicobacter* sp., *Kingella* sp., *Klebsiella* sp., *Kluyvera* sp., *Kozakia* sp., *Legionella* sp. *Leptonema* sp. *Leptotrichia* sp., *Levilinea* sp. *Luteimonas* sp. *Megamonas* sp., *Megasphaera* sp., *Meiothermus* sp., *Methylobacterium* sp., *Moraxella* sp., *Morganella* sp., *Mycoplasma* sp., *Neisseria* sp., *Nitrosomonas* sp., *Pectinatus* sp., *Pedobacter* sp., *Pelosinus* sp., *Propionispora* sp., *Proteus* sp., *Pseudomonas* sp., *Pseudoxanthomonas* sp., *Rickettsia* sp., *Salinibacter* sp., *Salmonella* sp., *Samsonia* sp., *Serratia* sp., *Shigella* sp., *Shimwellia* sp., *Sphingomonas* sp., *Stenotrophomonas* sp., *Thorselliaceae* sp., *Vampirococcus* sp., *Verminephrobacter* sp., *Vibrio* sp., *Victivallis* sp., *Vitreoscilla* sp., *Wolbachia* sp.

Additionally or alternatively, in some embodiments, the fungal infection is caused by a fungus selected from the group consisting of *Aspergillus* sp., *Aureobasidium* sp., *Candida* sp., *Cladosporium* sp., *Curvularia* sp., *Engodontium* sp., *Epicoccum* sp., *Gibberella* sp., *Hypocreales* sp., *Leptosphaerulina* sp., *Malessezia* sp., *Penicillium* sp., *Rhodosporidium* sp., *Trichosporon* sp., *Trichtophyton* sp., and *Ulocladium* sp.

Additionally or alternatively, in some embodiments, the wound comprises a biofilm and the wound dressing composition of the present technology prevents, reduces, inhibits, or disrupts the biofilm.

Additionally or alternatively, in some embodiments, the wound dressing composition is bioresorbable. Examples of bioresorbable materials include, but are not limited to, collagen, silk, polylactic acid (PLA), polyglycolic acid (PGA), polyanhydrides, polycaprolactones, poly(hydroxybutyrate) (PHB), poly(hydroxyvalerate) (PHV), and any combination thereof. Additionally or alternatively, in some embodiments, the wound dressing composition of the present technology is administered directly to the wound.

Any method known to those in the art for administering a wound dressing composition to an acute or a chronic wound disclosed herein may be employed. Suitable methods include in vitro or in vivo methods. In vivo methods typically include the administration of one or more wound dressing compositions to a subject in need thereof, suitably a human. When used in vivo for therapy, the one or more wound dressing compositions described herein are administered to the subject in effective amounts (i.e., amounts that have desired therapeutic effect). The dose and dosage regimen will depend upon the state of the wound of the subject, and the characteristics of the particular wound dressing composition used.

The effective amount may be determined during preclinical trials and clinical trials by methods familiar to physicians and clinicians. An effective amount of one or more wound dressing compositions useful in the methods may be administered to a subject in need thereof by any number of well-known methods for administering wound dressing compositions.

In some embodiments of the methods of the present technology, the wound dressing compositions are administered daily for 1 hour or more, for 2 hours or more, for 3 hours or more, for 4 hours or more, for 5 hours or more, for 6 hours or more, for 12 hours or more. Additionally or alternatively, in some embodiments of the methods of the present technology, the wound dressing compositions are administered one, two, three, four, or five times per day. Additionally or alternatively, in some embodiments of the methods of the present technology, the wound dressing compositions are administered daily for one, two, three, four or five weeks. Additionally or alternatively, in some embodiments of the methods of the present technology, the wound dressing compositions are administered daily for less than 6 weeks. Additionally or alternatively, in some embodiments of the methods of the present technology, the wound dressing compositions are administered daily for 6 weeks or more. Additionally or alternatively, in some embodiments of the methods of the present technology, the wound dressing compositions are administered daily for 12 weeks or more. Additionally or alternatively, in some embodiments of the methods of the present technology, the wound dressing compositions are administered every day, every other day, every third day, every fourth day, every fifth day, or every sixth day. Additionally or alternatively, in some embodiments of the methods of the present technology, the wound dressing compositions are administered weekly, bi-weekly, tri-weekly, or monthly. Additionally or alternatively, in some embodiments of the methods of the present technology, the wound dressing compositions are administered for a period of one, two, three, four, or five weeks. Additionally or alternatively, in some embodiments of the methods of the present technology, the wound dressing compositions are administered for six weeks or more. Additionally or alternatively, in some embodiments of the methods of the present technology, the wound dressing compositions are administered for twelve weeks or more. Additionally or alternatively, in some embodiments of the methods of the present technology, the wound dressing compositions are administered for a period of less than one year. Additionally or alternatively, in some embodiments of the methods of the present technology, the wound dressing compositions are administered for a period of more than one year.

In some embodiments of the methods of the present technology, the wound dressing composition can be changed for a chronic wound as appropriate. Additionally or alternatively, in some embodiments, the wound is a chronic wound selected from the group consisting of infectious wounds, venous ulcers, arterial ulcers, decubitis ulcers and diabetic ulcers. In some embodiments, the wound dressing protects the wound from infection. The infection may be a bacterial infection or a fungal infection. In some embodiments, the bacterial infection is caused by gram-negative or gram-positive bacteria.

Examples of gram-positive bacteria include, but are not limited to *Actinomyces* sp., *Arcanobacterium* sp., *Bacillus* sp., *Bavariicoccus* sp., *Brachybacterium* sp., *Clostridium* sp., *Cnuibacter* sp., *Corynebacterium* sp., *Enterococcus* sp., *Desulfitobacterium* sp., *Fervidobacterium* sp., *Georgenia* sp., *Janibacter* sp., *Lactobacillales* sp., *Microbispora* sp., *Nocardia* sp., *Pasteuria* sp., *Pilibacter* sp., *Propionibacterium* sp., *Rathayibacter* sp., *Rhodococcus* sp., *Roseburia* sp.,

*Rothia* sp., *Sarcina* sp., *Solibacillus* sp., *Sporosarcina* sp., *Staphylococcus* sp., *Streptococcus* sp., *Syntrophomonas* sp., or *Tepidibacter* sp.

Examples of gram-negative bacteria include, but are not limited to *Acetobacter* sp., *Acidaminococcus* sp., *Acinetobacter* sp., *Agrobacterium* sp., *Akkermansia* sp., *Anaerobiospirillum* sp., *Anaerolinea* sp., *Arcobacter* sp., *Armatimonas* sp., *Azotobacter* sp., *Bacteroides* sp., *Bacteroidetes* sp., *Bartonella* sp., *Bdellovibriosp.*, *Brachyspira* sp., *Bradyrhizobium* sp., *Caldilinea* sp., *Cardiobacterium* sp., *Christensenella* sp., *Chthonomonas* sp., *Coxiella* sp., *Cyanobacteria* sp., *Cytophaga* sp., *Dehalogenimonas* sp., *Desulfurobacterium* sp., *Devosia* sp., *Dialister* sp., *Dictyoglomus* sp., *Dinoroseobacter* sp., *Enterobacter* sp., *Escherichia* sp., *Fimbriimonas* sp., *Flavobacterium* sp., *Francisella* sp., *Fusobacterium* sp., *Gluconacetobacter* sp., *Haemophilus* sp., *Helicobacter* sp., *Kingella* sp., *Klebsiella* sp., *Kluyvera* sp., *Kozakia* sp., *Legionella* sp. *Leptonema* sp. *Leptotrichia* sp., *Levilinea* sp. *Luteimonas* sp. *Megamonas* sp., *Megasphaera* sp., *Meiothermus* sp., *Methylobacterium* sp., *Moraxella* sp., *Morganella* sp., *Mycoplasma* sp., *Neisseria* sp., *Nitrosomonas* sp., *Pectinatus* sp., *Pedobacter* sp., *Pelosinus* sp., *Propionispora* sp., *Proteus* sp., *Pseudomonas* sp., *Pseudoxanthomonas* sp., *Rickettsia* sp., *Salinibacter* sp., *Salmonella* sp., *Samsonia* sp., *Serratia* sp., *Shigella* sp., *Shimwellia* sp., *Sphingomonas* sp., *Stenotrophomonas* sp., *Thorselliaceae* sp., *Vampirococcus* sp., *Verminephrobacter* sp., *Vibrio* sp., *Victivallis* sp., *Vitreoscilla* sp., *Wolbachia* sp.

Additionally or alternatively, in some embodiments, the fungal infection is caused by a fungus selected from the group consisting of *Aspergillus* sp., *Aureobasidium* sp., *Candida* sp., *Cladosporium* sp., *Curvularia* sp., *Engodontium* sp., *Epicoccum* sp., *Gibberella* sp., *Hypocreales* sp., *Leptosphaerulina* sp., *Malessezia* sp., *Penicillium* sp., *Rhodosporidium* sp., *Trichosporon* sp., *Trichtophyton* sp., and *Ulocladium* sp.

Methods of Making the Wound Dressing of the Present Technology

In another aspect, the present disclosure provides a method for making a wound dressing composition of the present technology, wherein the method comprises providing a first layer comprising an effective amount of a homogeneous mixture of a collagen, an oxidized cellulose, and at least one bacteria reducing active ingredient, providing a second layer comprising an effective amount of a homogeneous mixture of a collagen, an oxidized cellulose, a silver compound, and at least one bacteria reducing active ingredient, and combining the first layer and the second layer to form the wound dressing composition. Additionally or alternatively, in some embodiments, the at least one bacteria reducing active ingredient of each of the first layer and of the second layer is mixed with a solvent, wherein the solvent is water, a ($C_1$-$C_3$)alcohol or an aqueous solution thereof. Additionally or alternatively, in some embodiments, the ($C_1$-$C_3$)alcohol comprises one or more of methanol, ethanol, propanol, isopropanol, or any combination thereof.

In some embodiments, the method may comprise adding a suitable amount of collagen (e.g., 1% or 2% solid content) to a solution of water or ethanol to form an intermediate slurry. Additionally or alternatively, in some embodiments, the method may comprise adding a suitable amount of collagen (e.g., 1% or 2% solid content) to a solution of ethanol to form an intermediate slurry. Additionally or alternatively, in some embodiments, the method may comprise adding a solution comprising the at least one bacteria reducing active ingredient as described herein (e.g., citric acid) to an intermediate slurry comprising collagen as described herein to form a slurry. The solution comprising the bacteria reducing active ingredient may be prepared by mixing a suitable amount of the bacteria reducing active ingredient, for example, in powdered form or liquid form, with a solvent, such as water or ethanol, to form the solution comprising the bacteria reducing active ingredient in a concentration such that the resultant slurry, after mixing, has an bacteria reducing active ingredient concentration as described herein, e.g., ≥about 50 mM to ≥about 400 mM. Additionally or alternatively, in some embodiments, the solution comprising the bacteria reducing active ingredient may be prepared by mixing a suitable amount of the bacteria reducing active ingredient, for example, in powdered form or liquid form, with a solvent, such as a ($C_1$-$C_3$)alcohol or an aqueous solution thereof, to form the solution comprising the bacteria reducing active ingredient in a concentration such that the resultant slurry, after mixing, has an bacteria reducing active ingredient concentration as described herein, e.g., ≥about 50 mM to ≥about 400 mM.

Additionally or alternatively, in some embodiments, the intermediate slurry may further comprise an anionic polysaccharide (e.g., ORC) as described herein in a suitable amount to maintain the solid content of the slurry. Additionally, the intermediate slurry may further comprise a metal (e.g., silver) as described herein in a suitable amount as described herein. At least a portion of the metal (e.g. silver) as described herein may be present as a complex of anionic polysaccharide with the metal, e.g., an ORC-silver complex. In some embodiments, this complex may be prepared by treating the anionic polysaccharide (e.g., ORC) with a solution of a metal salt (e.g., silver salt). The complex may comprise a salt formed between the anionic polysaccharide (e.g., ORC) and the metal ion (e.g., $Ag^+$). The metal salt solution may be an aqueous solution, and can be prepared in a quantity sufficient to provide the desired metal (e.g., silver) concentration as described herein in the resulting complex.

Anionic polysaccharides may behave as an ion exchanger, and can remove the metal ion (e.g., $Ag^+$) of a metal salt (e.g., silver salt) that contacts the anionic polysaccharides out of solution. The by-product of this exchange may be an acid from the salt and by using a salt of a weak organic acid, a weak acid may be produced which may not damage the polysaccharide. Using salts of strong acids such as sodium chloride or sodium sulfate produces hydrochloric acid or sulfuric acid by-products respectively, and these strong acids can cause damage such as depolymerization of the polysaccharide.

When using metal salts (e.g., silver salts) of weak acids, the metal ion (e.g., silver ion) may be exchanged for a proton on the polysaccharide and part of the salt is converted to weak acid. The mixture of acid and salt in the solution can result in a buffered solution which can maintain a fairly constant pH and can control the degree of neutralization. An equilibrium reaction may be established whereby the metal ions (e.g., silver ions) are bound to the acid portion of the polysaccharide and also to the salt molecules. This partitioning of the metal ions (e.g., silver ions) can prevent the neutralization of the polysaccharide from going to completion. Using a stoichiometric amount of, for example, silver acetate brings about a 65% to about a 75% degree of neutralization of the carboxylic acid groups on an oxidized cellulose polymer. This control of pH by creating a self-generating buffered solution and the use of methanol to control the swelling of the material can lead to a partially neutralized material in which the physical properties, e.g. tensile strength and shape of the polysaccharide, are preserved.

Additionally or alternatively, in some embodiments, the amount of metal salt (e.g., silver salt) used generally may be about equal to or up to twice the stoichiometric amount of carboxylic acid content of the polysaccharide. Additionally or alternatively, in some embodiments, a second charge of a stoichiometric amount of metal salt (e.g., silver salt) can be used if the reaction is recharged with fresh solvent and salt after the first charge reaches a constant pH. The material with elevated pH may then be washed to remove the excess metal salt (e.g., silver salt) and ions therefrom.

Additionally or alternatively, in some embodiments, the length of time that the anionic polysaccharide (e.g., ORC) may be treated with the metal salt solution is a period sufficient to incorporate the desired concentration of metal (e.g., silver) into the complex. For example, the anionic (e.g., ORC) may be treated with the metal salt solution for about 1 minute to about 120 minutes. Additionally or alternatively, in some embodiments, the treatment time may be about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 22 minutes, about 24 minutes, about 26 minutes, about 28 minutes, about 30 minutes, about 32 minutes, about 34 minutes, about 36 minutes, about 38 minutes, about 40 minutes, about 42 minutes, about 44 minutes, about 46 minutes, about 48 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, or any range including and/or in between any two of the preceding values. Generally, the length of time necessary will depend on the anionic polysaccharide used and can be easily determined by the skilled person.

In some embodiments, the anionic-polysaccharide-metal complex (e.g., ORC-silver complex) may be mixed with a further anionic polysaccharide as described herein, e.g. anionic polysaccharides that have not been complexed with a metal, as well as collagen to form the intermediate slurry. In particular, the further anionic polysaccharide may be ORC.

Additionally or alternatively, in some embodiments, the collagen may be contacted with an acid solution, e.g., in order to swell the collagen. Examples of suitable acid solutions include, but are not limited to acetic acid and/or ascorbic acid. For example, the collagen may be contacted with the acid solution prior to forming the intermediate slurry with the anionic-polysaccharide-metal complex (e.g., ORC-silver complex) and optionally, the further anionic polysaccharide (e.g., ORC) and/or prior to adding the solution comprising the bacteria reducing active ingredient (e.g., citric acid) to the intermediate slurry.

Additionally or alternatively, in some embodiments, the method may further comprise adding a plasticizer, such as, but not limited to glycerol or polyvinylpyrrolidone, in a suitable amount. For example, the plasticizer may be added to the intermediate slurry and/or to the biomaterial slurry.

Additionally or alternatively, in some embodiments, the methods may comprise contacting the collagen with an acid solution comprising (i) citric acid or (ii) citric acid and acetic acid in suitable amounts to form a swelled collagen. The swelled collagen may then be combined with an anionic polysaccharide (e.g., ORC) and a metal (e.g., silver) in suitable amounts to form the slurry. As discussed above, at least a portion of the metal (e.g. silver) as described herein may be present as a complex of anionic polysaccharide with the metal, e.g., an ORC-silver complex. The complex of anionic polysaccharide with the metal (e.g., an ORC-silver complex) may be prepared as discussed above. In some embodiments, the swelled collagen may then be combined with an anionic-polysaccharide-metal complex (e.g., ORC-silver complex) and optionally, a further anionic polysaccharide (e.g., ORC) as described herein in suitable amounts to form the slurry. In some embodiments, the method may further comprise adding a plasticizer, such as, but not limited to glycerol or polyvinylpyrrolidone, in a suitable amount. For example, the plasticizer may be combined with the swelled collagen, the anionic polysaccharide (e.g., ORC) and/or the metal (e.g., silver).

Additionally or alternatively, in some embodiments, the methods described herein may further comprise drying or dehydrating the slurry, e.g., to form a sponge or a film. Drying may comprise freeze-drying or solvent-drying of the slurry. Freeze-drying may comprise the steps of freezing the slurry, followed by evaporating the solvent from the frozen slurry under reduced pressure. Suitably, a method of freeze-drying is similar to that described for a collagen-based sponge in U.S. Pat. No. 2,157,224, the entire content of which is incorporated herein by reference. Additionally or alternatively, in some embodiments, the freeze-drying may be performed in stages to prepare the multi-layered configurations described herein. Additionally or alternatively, in some embodiments, a first layer comprising any embodiment disclosed herein may be frozen at a suitable temperature until solid, for example about −80° C. A second layer comprising any embodiment disclosed herein may be added adjacent to the first layer by repeating the process until a desired composition is achieved. The resultant multi-layered configuration may be freeze-dried as described above.

Additionally or alternatively, in some embodiments, solvent-drying may comprise freezing the slurry, followed by immersing the slurry in a series of baths of a hygroscopic organic solvent such as anhydrous isopropanol to extract the water from the frozen slurry, followed by removing the organic solvent by evaporation. Methods of solvent drying are described, for example, in U.S. Pat. No. 3,157,524, the entire content of which is incorporated herein by reference.

Additionally or alternatively, in some embodiments, to form a film as described herein, the slurry as prepared as described herein, may be placed in a dehydration oven, which may evaporate water and/or solvent using a suitably higher temperature with or without circulation of air through a chamber containing a desiccant or the like.

Additionally or alternatively, in some embodiments, the methods may further comprise treating the slurry, or the dried wound dressing composition, with a cross-linking agent such as epichlorhydrin, carbodiimide, hexamethylene diisocyanate (HMDI) orglutaraldehyde. Alternatively, cross-linking may be carried out dehydrothermally. The method of cross-linking can affect the final product, (e.g., HMDI cross-links the primary amino groups on collagen, whereas carbodiimide cross-links carbohydrate on the ORC to primary amino groups on the collagen).

Kits Comprising the Wound Dressing of the Present Technology

In a further related aspect, the present disclosure provides kits that include a wound dressing composition of any embodiment described herein and instructions for use. The kit may optionally include instructions for generating a wound dressing composition of any embodiment described herein. The kits of the present technology may also include instructions for treating a wound in a subject in need thereof. The kit may optionally comprise components such as antiseptic wipes, ointment, adhesive tape, tweezers, scissors, etc.

EXAMPLES

The present technology is further illustrated by the following Example, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology.

Example 1: Making the Wound Dressing Compositions of the Present Technology

As shown in Table 1 (below), milled collagen powder was added to either water or ethanol, and mixed in a blender to form a mixture with either a 1% (standard density) or 2% (double density) solid content (0.55 g or 1.1 g per 100 ml). ORC (0.45 g or 0.90 g per 100 ml) was then added to the mixture and blended to form intermediate slurries, while maintaining the solid content. Citric acid was then added in an appropriate amount to achieve a desired final concentration of about 100 mM to about 400 mM of citric acid in the intermediate slurry. A portion (31 g) of each of the slurries was transferred into 10×10 cm square plates and spread evenly before being frozen at −80° C. overnight and freeze-dried for 24 hours to prepare a sponge. As depicted in Table 1, sponges manufactured by dissolving the citric acid in ethanol rather than water dramatically reduced the the shrinkage that occurs when the foam was removed from the freeze-drier. The results demonstrate the tackiness of the wound dressing composition was also significantly reduced compared to wound dressing compositions prepared with water as the solvent.

facing side of the first layer contacting the wound. A first biofilm level will be determined using the colony drip flow reactor (C-DFR), described herein. A second biofilm level will be determined 24 hours after administering the wound dressing composition to the wound. It is anticipated that administration of the wound dressing composition to a chronic wound will result in the prevention, reduction, inhibition, or disruption of biofilm levels in the wound. It is anticipated that the treated subjects will not experience silver-associated toxicity.

These results will demonstrate that the wound dressing compositions of the present technology are useful for preventing, reducing, inhibiting, or disrupting biofilm levels in a wound in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed

| Prototype | Milled Collagen* | ORC Powder | ORC Powder w/Silver | Citric Acid Concentration (mM) | Citric Acid Solvent | Tacky | Shrinkage |
|---|---|---|---|---|---|---|---|
| 1 | √ | √ | √ | 100-400 | Water | XXXX | XXXX |
| 2 | √ | √ | √ | 100-400 | Ethanol | XX | XX |
| 3 | √ | √ |   | 100-400 | Water | XXXX | XXXX |
| 4 | √ | √ |   | 100-400 | Ethanol | XX | XX |

*Milled collagen is obtained from milling of bovine hides following alkalinization
X = none,
XX = minimal,
XXX = moderate,
XXXX = severe Example 2: Preventing and Treating Biofilm Formation in a Wound The wound dressing composition described herein will be administered directly to a chronic wound, with the wound-herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A wound dressing composition comprising a first layer and a second layer:
   wherein the first layer comprises a homogeneous mixture of a collagen, an oxidized cellulose, and at least one bacteria reducing active ingredient;
   wherein the second layer comprises a homogeneous mixture of a collagen, an oxidized cellulose, a silver compound, and at least one bacteria reducing active ingredient;
   wherein the at least one bacteria reducing active ingredient of each of the first layer and of the second layer is citric acid,
   wherein the at least one bacterial reducing active ingredient of each of the first layer and the second layer is mixed with a solvent, wherein the solvent consists of ethanol, and
   wherein the first layer and the second layer are each in the form of a freeze-dried sponge.

2. The wound dressing composition of claim 1, wherein the citric acid is present in each of the first layer and the second layer at a concentration of about 50 millimolar to about 400 millimolar.

3. The wound dressing composition of claim 1, further comprising a third layer and a fourth layer, wherein the third layer and the fourth layer each comprise a homogeneous mixture of a collagen, an oxidized cellulose, and a silver compound.

4. The wound dressing composition of claim 3, wherein the oxidized cellulose of each of the first layer, the second layer, the third layer, and the fourth layer comprises oxidized regenerated cellulose (ORC), and wherein the wound dressing composition is bioresorbable.

5. The wound dressing composition of claim 4, wherein the oxidized cellulose comprises about 30 wt. % to about 70 wt. % of each of the first layer, the second layer, the third layer, and the fourth layer, wherein the oxidized cellulose has a weight-average molecular weight of about 10,000 to about 1,000,000, and wherein the oxidized cellulose of each of the first layer, the second layer, the third layer, and the fourth layer comprises fiber lengths of about 5 micrometers to about 1,000 micrometers.

6. The wound dressing composition of claim 3, wherein the collagen of each of the first layer, the second layer, the third layer, and the fourth layer is a mammalian collagen, wherein the mammalian collagen is selected from the group consisting of a bovine collagen, a human collagen, a recombinantly derived collagen, and any combination thereof, wherein the mammalian collagen comprises about 0.1 wt. % to about 60 wt. % of each of the first layer, the second layer, the third layer, and the fourth layer, and wherein the mammalian collagen has a weight-average molecular weight of about 5,000 to about 100,000.

7. The wound dressing composition of claim 4, wherein a ratio of collagen to ORC in each of the first layer, the second layer, the third layer, and the fourth layer is in a range of about 60:40 to about 40:60.

8. The wound dressing composition of claim 3, wherein the silver compound comprises about 0.1 wt. % to about 1 wt. % of each of the second layer, the third layer, and the fourth layer.

9. The wound dressing composition of claim 8, wherein the silver compound of each of the second layer, the third layer, and the fourth layer comprises one or more pharmaceutically acceptable silver salts, and wherein the one or more pharmaceutically acceptable silver salts are selected from the group consisting of silver oxide, silver chromate, silver allantoinate, silver borate, silver glycerolate, silver nitrate, silver acetate, silver chloride, silver sulfate, silver lactate, silver bromide, silver iodide, silver carbonate, silver citrate, silver laurate, silver deoxycholate, silver salicylate, silver p-aminobenzoate, silver p-aminosalicylate, nanocrystalline silver, any pharmaceutically acceptable salt thereof, and any combination thereof.

10. The wound dressing composition of claim 3, wherein each of the first layer, the second layer, the third layer, and the fourth layer comprise one or more biomaterials, and wherein the one or more biomaterials are selected from the group consisting of gelatin, chitosan, fibronectin, hyaluronic acid, polysaccharides, and any combination thereof.

11. The wound dressing composition of claim 3, wherein each of the first layer, the second layer, the third layer, and the fourth layer comprise at least one plasticizer, wherein the at least one plasticizer comprises about 1 wt. % to about 10 wt. % of each of the first layer, the second layer, the third layer, and the fourth layer, and wherein the at least one plasticizer is selected from the group consisting of an acetylated monoglyceride, an alkyl citrate, methyl ricinoleate, glycerol, and any combination thereof.

12. The wound dressing composition of claim 11, wherein the at least one plasticizer is alkyl citrate, and wherein the alkyl citrate is triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, or any combination thereof.

13. The wound dressing composition of claim 3, wherein the first layer has a solids content of about 0.1 wt. % to about 5 wt. %, wherein the second layer has a solids content of about 2 wt. % to about 10 wt. %, and wherein each of the third layer and the fourth layer have a solids content of about 0.1 wt. % to about 10 wt. %.

14. The wound dressing composition of claim 3, wherein each of the first layer, the second layer, the third layer, and the fourth layer comprise a wound-facing side and an environmental-facing side, and wherein the wound-facing side of the fourth layer is coupled with the environmental-facing side of the third layer, the wound-facing side of the third layer is coupled with the environmental-facing side of the second layer, and wherein the wound-facing side of the second layer is coupled with the environmental-facing side of the first layer.

15. A method for making a wound dressing comprising:
   a. providing a first layer comprising an effective amount of a homogeneous mixture of a collagen, an oxidized cellulose, and at least one bacteria reducing active ingredient;
   b. providing a second layer comprising an effective amount of a homogeneous mixture of a collagen, an oxidized cellulose, a silver compound, and at least one bacteria reducing active ingredient; and c. combining the first layer and the second layer to form the wound dressing composition, wherein the at least one bacteria reducing active ingredient of each of the first layer and of the second layer is citric acid, and wherein the at least one bacteria reducing active ingredient of each of the first layer and of the second layer is mixed with a solvent, wherein the solvent consists of ethanol, and wherein the first layer and the second layer are each in the form of a freeze-dried sponge.

16. The wound dressing composition of claim 1, wherein the citric acid is present in each of the first layer and the second layer at a concentration of about 100 Millimolar to about 400 Millimolar.

* * * * *